United States Patent
Chung

(10) Patent No.: US 8,946,295 B2
(45) Date of Patent: *Feb. 3, 2015

(54) HISTONE HYPERACETYLATING AGENTS FOR PROMOTING WOUND HEALING AND PREVENTING SCAR FORMATION

(75) Inventor: Yih-Lin Chung, Taipei (TW)

(73) Assignee: Sunny Pharmtech Inc., New Taipei (TW)

( * ) Notice: Subject to any disclaimer, the term of this patent is extended or adjusted under 35 U.S.C. 154(b) by 1361 days.

This patent is subject to a terminal disclaimer.

(21) Appl. No.: 10/843,025

(22) Filed: May 10, 2004

(65) Prior Publication Data
US 2007/0072793 A1 Mar. 29, 2007

Related U.S. Application Data

(63) Continuation-in-part of application No. 10/205,738, filed on Jul. 25, 2002, now Pat. No. 6,809,118.

(51) Int. Cl.
| A61K 31/192 | (2006.01) |
| A61K 31/19 | (2006.01) |
| A61K 31/351 | (2006.01) |
| A61K 31/166 | (2006.01) |
| A61K 38/12 | (2006.01) |

(52) U.S. Cl.
CPC ............... *A61K 38/12* (2013.01); *A61K 31/19* (2013.01); *A61K 31/192* (2013.01); *Y10S 514/928* (2013.01)
USPC ........... 514/619; 514/568; 514/629; 514/459; 514/928

(58) Field of Classification Search
None
See application file for complete search history.

(56) References Cited

U.S. PATENT DOCUMENTS

| 4,218,478 | A | * | 8/1980 | Omura et al. ............. 514/619 |
| 5,281,623 | A | | 1/1994 | Clemens et al. |
| 5,430,064 | A | | 7/1995 | Hirsch et al. |
| 5,605,930 | A | | 2/1997 | Samid |
| 5,877,213 | A | | 3/1999 | Samid |
| 5,993,845 | A | | 11/1999 | Geerts et al. |
| 6,124,495 | A | | 9/2000 | Neiss et al. |
| 6,225,294 | B1 | | 5/2001 | Daifotis et al. |
| 6,313,091 | B1 | | 11/2001 | Wisniewski et al. |
| 6,403,555 | B1 | | 6/2002 | Skov |
| 6,538,030 | B2 | | 3/2003 | Chung et al. ............. 514/570 |
| 6,548,479 | B1 | | 4/2003 | Skov |
| 2001/0009922 | A1 | | 7/2001 | Faller |
| 2001/0012513 | A1 | * | 8/2001 | Robl et al. ............. 424/93.21 |
| 2001/0021700 | A1 | | 9/2001 | Moore et al. |
| 2002/0055542 | A1 | * | 5/2002 | Chung et al. ............. 514/570 |
| 2002/0183388 | A1 | * | 12/2002 | Gudas et al. ............. 514/559 |
| 2003/0082666 | A1 | | 5/2003 | Kammer et al. |
| 2003/0114525 | A1 | | 6/2003 | Kammer et al. |
| 2003/0134865 | A1 | | 7/2003 | Adcock et al. |
| 2003/0147926 | A1 | | 8/2003 | Ebert et al. |
| 2003/0235588 | A1 | * | 12/2003 | Richon et al. |
| 2004/0029922 | A1 | * | 2/2004 | Lan-Hargest et al. |
| 2005/0171206 | A1 | | 8/2005 | Brahe et al. |
| 2006/0251689 | A1 | | 11/2006 | Weidner |

FOREIGN PATENT DOCUMENTS

| WO | WO 98/00127 | * | 1/1998 |
| WO | WO 98/29109 | | 9/1998 |
| WO | WO 01/17514 | | 3/2001 |

OTHER PUBLICATIONS

"Influence of Washing Steps on Cell Attachment: Comparison of PDL-coated and Cell Culture Treated Microplates," Biocompare: The Buyer's Guide for Life Scientists, http://www.biocompare.com/Articles/ApplicationNote/1605/Influence-Of-Washing-Steps-On-Cell-Attachment-Comparison-Of-PDL-coated-And-Cell-Culture-Treated-Microplates.html.*
Mayo Clinic, "Psoriasis: Causes", downloaded on Nov. 16, 2013 from "http://www.mayoclinic.com/health/psoriasis/DS00193", 13 pages.*
U.S. Appl. No. 09/938,926, Chung et al.
ADR news, Phenytoin. Stevens-Johnson syndrome: case report, Serious Reactions (ADR news), Feb. 22, 1996, ADISNEWS. See: abstract.
Merck Index, Ninth Edition, 1976, pp. 137 and 1273.
Danesi, Romano et al., "Pharmacogenetic Determinants of Anti-Cancer Drug Activity and Toxicity," *TRENDS in Pharmacological Sciences*, 22(8):420-426 and 420(Abstract, particularly) (2001).
Shufeng, Z., et al., "5,6-Dimethylxanthenone-4-acetic acid (DMXAA): A New Biological Response Modifier for Cancer Therapy," *Investigational New Drugs*, 20:281-295 (2002).
Chung et al. "Antitumor histone deacetylase inhibitors suppress cutaneous radiation syndrome: implications for increasing therapeutic gain in cancer radiotherapy" Molecular Cancer Therapeutics 2004;3(3):317-325.
Goldman, Lee, et al., Cecil Textbook of Medicine, vol. 1, pp. 1061-1074, 21$^{st}$ ed. (2000).
Mishra et al., "Histone Deacetylase Inhibitor Trichostatin A as a Strong Candidate for Treatment of Systemic Lupus Erythematosus," FASEB Journal, 5:A1214, Mar. 2001.
Mishra et al., "Trichostatin A Reverses Skewed Expression of CD154, Interleukin-10, and Interferon-Gamma Gene and Protein Expression in Lupus T Cells," Proceedings of the National Academy of Sciences of USA 98(5):2628-2633, (2001).
Richon et al., "Histone Deacetylase Inhibitor Selectively Induces P21 WAF1 Expression and Gene-Associated Histone Acetylation," PNAS, 97(18):10014-10019, Aug. 28, 2000.

(Continued)

*Primary Examiner* — Savitha Rao
*Assistant Examiner* — Gregg Polansky
(74) *Attorney, Agent, or Firm* — Cesari and McKenna, LLP

(57) ABSTRACT

A method for promoting wound healing and preventing scar formation in a variety of wounds in skin, mucosa, and cornea. The method comprises administering a therapeutically effective amount of a histone deacetylase inhibitor or a hyperacetylating agent. The histone deacetylase inhibitor or hyperacetylating agent is capable of stimulating multiple cytokines/growth factors in the early phase of wound healing, and suppressing fibrogenic cytokines/growth factors in the late phase of tissue remodeling in the wound site, and is useful in promoting epithelial cell re-growth and reducing excessive collagen accumulation, which results in rapid wound closure with reduced scaring.

15 Claims, 22 Drawing Sheets

(56) References Cited

OTHER PUBLICATIONS

Witt et al., "Induction of Fetal Hemoglobin Expression by the Histone Deacetylase Inhibitor Apicdin," Blood 101(5), Mar. 1, 2003.
www.merriam-webster.com/dictionary/prevent, Nov. 13, 2007.
Goldring et al., Mechanisms of Bone Loss in Inflammatory Arthritis: Diagnosis and Therapeutic Implications, Arthritis Res 2000, 2:33-37.
Stoilov et al.,"Inhibition of Repair of X-ray-induced DNA Double-Strand Breaks in Human Lymphocytes Exposed to Sodium Butyrate," *International Journal of Radiation Biology* vol. 76, No. 11, pp. 1485-1491 (2000).
Miller et al., "Modulation of Radiation Response of Human Tumour Cells by the Differentiation Inducers, Phenylacetate and Phenylbutyrate," *International Journal of Radiation Biology* vol. 72, No. 2, pp. 211-218 (1997).
Saunders et al., "Histone Deacetylase Inhibitors as Potential Anti-Skin Cancer Agents," *Cancer Research* vol. 59, pp. 399-404 (1999).

\* cited by examiner 1  2  3  4

Acetylated H3

Coomassie stain

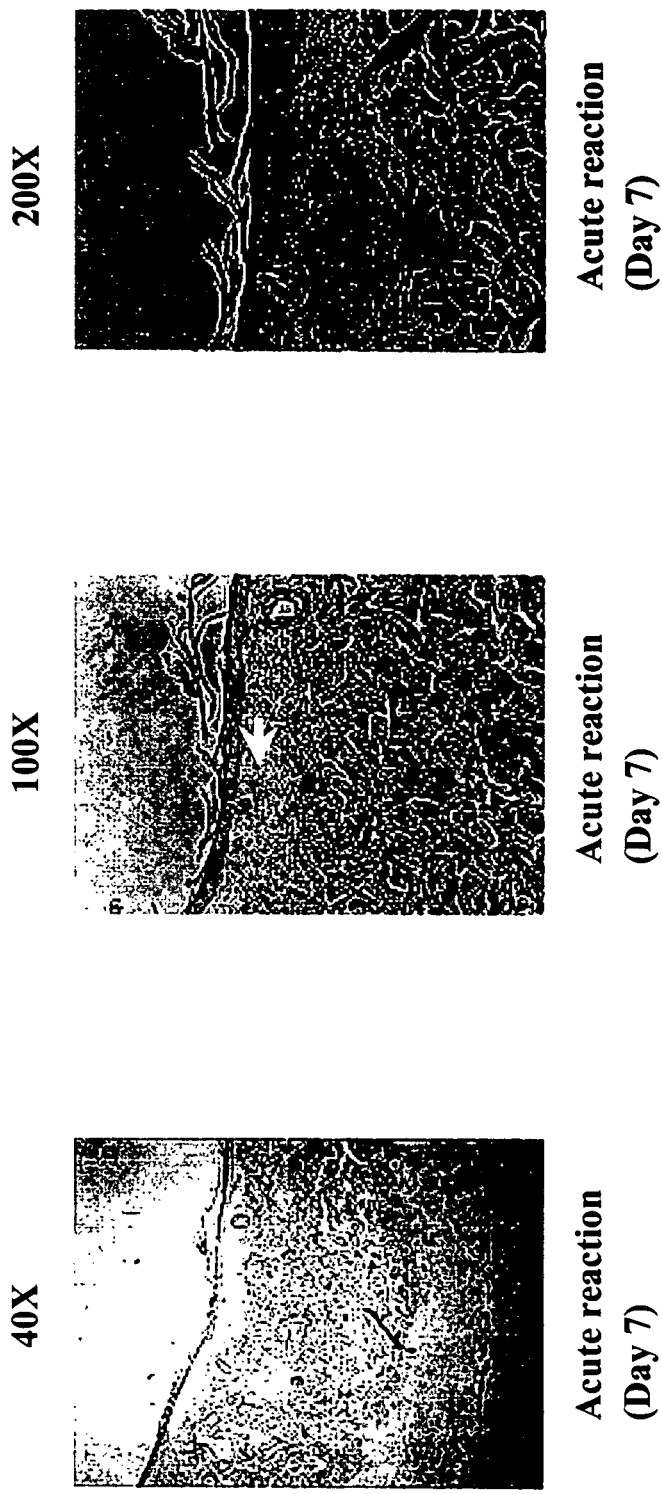

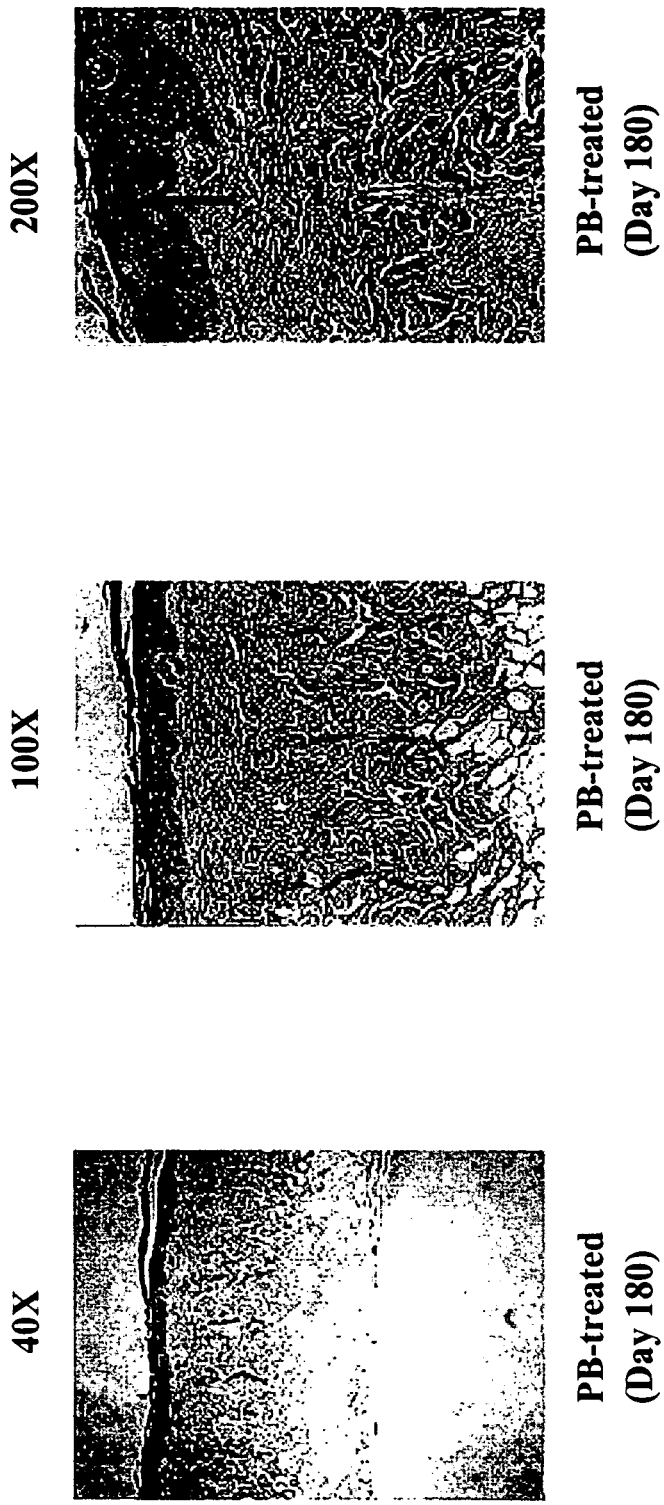

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
cgggtggcag gcgagagc                                                    18

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
catgcactac tgtgtgct                                                    18

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggaattgttg ctatatttct gc                                               22

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
ccgaggactt tagctgca                                                    18
```

HISTONE HYPERACETYLATING AGENTS FOR PROMOTING WOUND HEALING AND PREVENTING SCAR FORMATION

This application is a continuation in part of U.S. patent application Ser. No. 10/205,738 filed Jul. 25, 2002 now U.S. Pat. No. 6,809,118.

BACKGROUND OF THE INVENTION

1. Field of the Invention

The present invention relates to the treatment of a wide variety of wounds. More particularly, the present invention relates to a method and pharmaceutical composition for not only accelerating wound healing but also preventing scar formation in skin, mucosa, and cornea.

2. Description of the Related Art

The primary function of the skin, mucosa and cornea is to serve as a protective barrier against the environment. Loss of the integrity of large portions or large wound of the skin, mucosa, or cornea as a result of injury or illness may lead to major disability or even death. Complications are a constant risk with wounds that have not fully healed and remain open for extended periods of time. On the other hand, over-repair with excess collagen accumulation will cause cosmetic problems and decreased tensile strength. Thus, it would be beneficial to accelerate the wound healing process but not to exaggerate the tissue remodeling response. However, present methods for both promoting wound healing and preventing scar formation are inadequate or ineffective.

Wound healing is a dynamic, interactive process involving soluble mediators, blood cells, extracellular matrix, and parenchymal cells. Wound healing has three phases, inflammation, tissue formation, and tissue remodeling. These phases overlap in time and are spatially triggered by many cytokines and growth factors differentially secreted from the recruited blood cells and parenchymal cells around the wound space (Clark, R. A. F. The molecular and cellular biology of wound repair. 2nd ed. New York:plenum Press, 1996).

In the first wound healing phase (inflammation), tissue injury causes the disruption of blood vessels and extravasation of blood constituents, which activate the clotting cascade and lead to hemostasis. The platelets forming clots release a number of vasoactive compounds and growth factors such as PDGF that attracts and activates macrophages and fibroblasts. Adherence of activated macrophages to the extracellular matrix further releases other chemoattractants such as GM-CSF, and TNF-α to recruit inflammatory leukocytes to the sites of injury. Infiltrating neutrophils cleanse the wound area of foreign particles and bacteria and are then extruded with the eschar or phagocytosed by macrophages.

In the second healing phase (tissue formation) beginning in the wound site three to four days after the injury, activated macrophages digest devitalized collagen and the fibrin clot. Dissolution of the clot allows the movement of more macrophages, fibroblasts and blood vessels to form the granulation tissue. Local release of growth factors such as EGF, TGF-α, and KGF from fibroblasts, macrophages, platelets, and epidermal cells stimulate the process. The activated macrophages also provide a continuing source of growth factors such as TGF-β, and VEGF necessary to further stimulate fibroplasias and angiogenesis. Thus, the stage is marked by not only the formation of new blood vessels to sustain the newly formed granulation tissue but also the proliferation of fibroblasts and their migration into the wound site where they produce an extracellular matrix, known as ground substance, comprised of collagen, fibronectin, and hyaluronic acid to replace the digested clot. On the other hand, re-epithelialization occurs during this stage of wound healing. Epithelial cells proliferate at the wound edges and migrate across the ground substance that serves as a scaffold upon which endothelial cells, fibroblasts and macrophages are also able to move. Migration is then halted by contact inhibition among epithelial cells, which at this point divide and differentiate to reconstitute the epithelium. In addition to re-epithelialization, the myofibroblasts derived through the differentiation of resident fibroblasts after TGF-β stimulation also use the newly deposited extracellular matrix to contract and promote more rapid wound closure. The contraction probably requires stimulation by TGF-β1 or TGF-β2 and PDGF.

In the third healing phase (tissue remodeling), collagen and matrix remodeling begin when granulation tissue formation begins and continues long after the wound has been covered by new epithelium and can continue for more than 1 year. This final stage of wound healing is characterized by devascularization and the replacement of granulation tissue and cells with a matrix comprised predominantly of type I collagen. Collagen remodeling during the transition from granulation tissue to scar is dependent on the continued synthesis and catabolism of collagen, and on the continued TGF-β stimulation. The degradation of collagen in the wound is controlled by several proteolytic enzymes termed matrix metalloproteinase, which are secreted by macrophages, epidermal cell, and endothelial cells, as well as fibroblasts. The various phases of wound repair rely on distinct combinations of matrix metalloproteinases, tissue inhibitors of metalloproteinase, and cytokines and growth factors.

In the wound healing processes, a variety of growth factors (such as EGF, FGF, KGF, PDGF, GM-CSF, TGF-α, TGF-β1, TGF-β2, TGF-β3, TNF-α, VEGF, IGF, IL-1) play pivotal roles in the transition from inflammation, tissue formation to tissue remodeling. However, the overall clinical experience with growth factors to accelerate wound healing has been discouraging. This is not surprising, considering that wound repair needs combinations of various growth factor stimulations, and a complex set of interactions among growth factors, blood elements, extracellular matrix, and cells. On the other hand, over-expression of TGF-β1, TGF-β2, IGF, or IL-1 may cause over-repair and excess accumulation of collagen within the wound, which results in scar formation and fibrosis, for example, hypertrophic scars, keloids, and radiation-induced fibrosis. Thus, in order to accelerate wound healing and to prevent scar formation or over-repair, it is necessary to stimulate the host to produce a variety of cytokines and growth factors in the early wound healing processes (inflammation and tissue formation) but to suppress the stimulation of cytokines and growth factors in the late wound healing process (tumor remodeling).

The primary goals of the treatment of wounds are rapid wound closure and a functional and aesthetically satisfactory scar.

SUMMARY OF THE INVENTION

The present invention provides a method and pharmaceutical composition for promoting wound healing and preventing scar formation in a subject. The pharmaceutical composition comprises a treatment effective amount of a histone hyperacetylating agent or a pharmaceutically acceptable salt thereof and a pharmaceutically acceptable carrier. The method comprises administrating the pharmaceutical composition to a subject.

The purpose of the method and pharmaceutical composition of the present invention includes (1) stimulating the host to produce a variety of cytokines and growth factors to accelerate the healing in a variety of wounds in skin, mucosa, or cornea, and (2) preventing the fibroproliferative disorders or scar formation due to excess accumulation of collagen within the wound during tissue remodeling.

According to the present invention, it was surprisingly found that the pharmaceutical composition containing the histone deacetylase inhibitor stimulated the expression of multiple growth factors such as TGF-$\beta$1, TGF-$\beta$2, and TNF-$\alpha$ in the early phase of wound healing, and suppressed them in the later phase of wound healing, which resulted in both accelerating wound healing and ameliorating scar formation.

The compounds of the present invention can be administered intravenously, enterally, parentally, intramuscularly, intranasally, subcutaneously, topically or orally. The dosage amounts are based on the effective concentration observed in vitro and in vivo studies. The varied and efficacious utility of the compounds of the present invention is further illustrated by the discovery that they may also be administered concomitantly or in combination with a cytokine, an interleukin, a growth factor, an angiogenic agent, an anti-neoplastic agent, an anti-inflammatory agent, a steroid, an analgesic agent, an antipruritic agent, an antibacterial agent, an antiviral agent, an antifungal agent, an antiparasitic agent, an anti-oxidant agent, retinoic acid, an vasoactive agent, an adenosine receptor agonist, and a peroxisome proliferating activator receptor (PPAR) agonist.

BRIEF DESCRIPTION OF THE DRAWINGS

The present invention will be more fully understood and further advantages will become apparent when reference is made to the following description of the invention and the accompanying drawings in which:

FIG. 1C shows normal skin without irradiation; FIG. 1D shows irradiated skin without any treatment; FIG. 1E shows irradiated skin treated with the vehicle; and FIG. 1F shows irradiated skin treated with the 1% PB cream.

FIGS. 3A-3L are the H&E histology photographs showing that the topical histone deacetylase inhibitors have effects on suppressing the radiation-induced skin damage. 3A, 3D, 3G, and 3J are H&E histology at 40× field; 3B, 3E, 3H, and 3K are H&E histology at 100× field; 3C, 3F, 3I, and 3L are H&E histology at 200× field. FIGS. 3A-3C are of normal skin. FIGS. 3D-3F are of acute reaction on Day 7 after irradiation, showing subepithelial swelling (white arrow). FIGS. 3G-3I are of the vehicle group on Day 180, showing thinner epithelium, subepithelium swelling, increased vessel and skin appendage density, and thick dermis with more collagen deposit. The black arrowheads indicate that the subcutaneous fat layer in the vehicle group was replaced by fibrous tissues and appendages. FIGS. 3J-3L are of the histone deacetylase inhibitor treated group on Day 180, showing thicker epidermis with 10-30 cell layers (black arrow), less subepithelial swelling, a thinner dermis with less collagen deposition, and few skin appendages. a indicates epidermis, b indicates dermis, and c indicates subcutaneous tissue.

FIG. 4A shows the changes of TGF-$\beta$1 levels after irradiation treated with or without the topical phenylbutyrate (PB). FIG. 4B shows the changes of TGF-$\beta$2 levels after irradiation treated with or without the topical phenylbutyrate (PB). FIG. 4C shows the changes of TGF-$\beta$3 levels after irradiation treated with or without the topical phenylbutyrate (PB). FIG. 4D shows the changes of TNF-$\alpha$ levels after irradiation treated with or without the topical phenylbutyrate (PB).

FIG. 5A is of normal skin stained with TGF-beta. FIG. 5B is a picture of acute dermatitis on Day 7 after irradiation without any drug treatment, showing that TGF-beta was up-regulated. FIG. 5C is of the vehicle group on Day 180 after irradiation, showing that the expression of TGF-beta was increased with time, persistent and highly expressed in fibrogenic skin both in keratinocytes of the epidermis and in myofibroblasts of the dermis. FIG. 5D is of the PB treated-group on Day 180 after irradiation, showing that the topical PB suppressed the TGF-beta expression effectively, which correlates well with less collagen fiber accumulation in dermis and more cell layers in epithelium since TGF-beta triggers fibroblast proliferation but inhibits epithelial cell growth. In the figure, a indicates epidermis, b indicates dermis, and c indicates subcutaneous tissue.

FIG. 6A is of normal skin for TNF-alpha staining. FIG. 6B is of the PB treated-group on Day 270 after irradiation, showing that the histone deacetylase inhibitor suppressed the TNF-$\alpha$ expression effectively, which correlates well with less inflammatory cell infiltration and no chronic ulceration. FIG. 6C is an irradiated skin treated with Vaseline, showing that TNF-$\alpha$ was up-regulated in the subcutaneous tissue with ulcerations on Day 270 (the arrow indicates the necrotic wound). FIG. 6D is an irradiated skin treated with vehicle, showing that TNF-$\alpha$ was up-regulated in the subcutaneous tissue with heavy inflammatory cell infiltrates on Day 270. In the figure, b indicates dermis, and c indicates subcutaneous tissue.

FIG. 8A shows time-course (0, 4, and 24 hours) analysis of the up-regulated levels of p21Cip1 protein, a cell-cycle inhibitor, in BNL 1MEA7R.1 carcinoma cells during treatment with 4 mM PB. FIG. 8B shows an initial tumor size of 1MEA7R.1 beneath the skin about 0.5 cm in dimension before treatment; FIG. 8C shows the skin ulcer and necrosis due to tumor growth in a placebo- or vehicle-treated group at week 4; FIG. 8D shows PB decreases the skin wound from tumor invasion in the PB-treated group at week 4.

FIG. 9A is the paw treated with TSA, which promotes the wound healing in the bacterial injection site in the plantar region; FIG. B is the paw treated with vehicle (white arrow indicates the ulcer resulting from the injection of killed *Mycobacterium tuberculosis* with 0.3 mg in 0.1 ml of light mineral oil and complete Freund's Adjuvant).

FIG. 10A shows TSA 1 nM for 48 hours up-regulated the EBV thymidine kinase activity in EBV-positive Daudi cells. FIG. 10B shows that the combination of TSA and GCV, or TSA, GCV and radiation produces selective cell death of EBV-positive cells. Bars represent the mean of three different experiments performed in triplicate.

DETAILED DESCRIPTION OF THE INVENTION

Figure 1A:
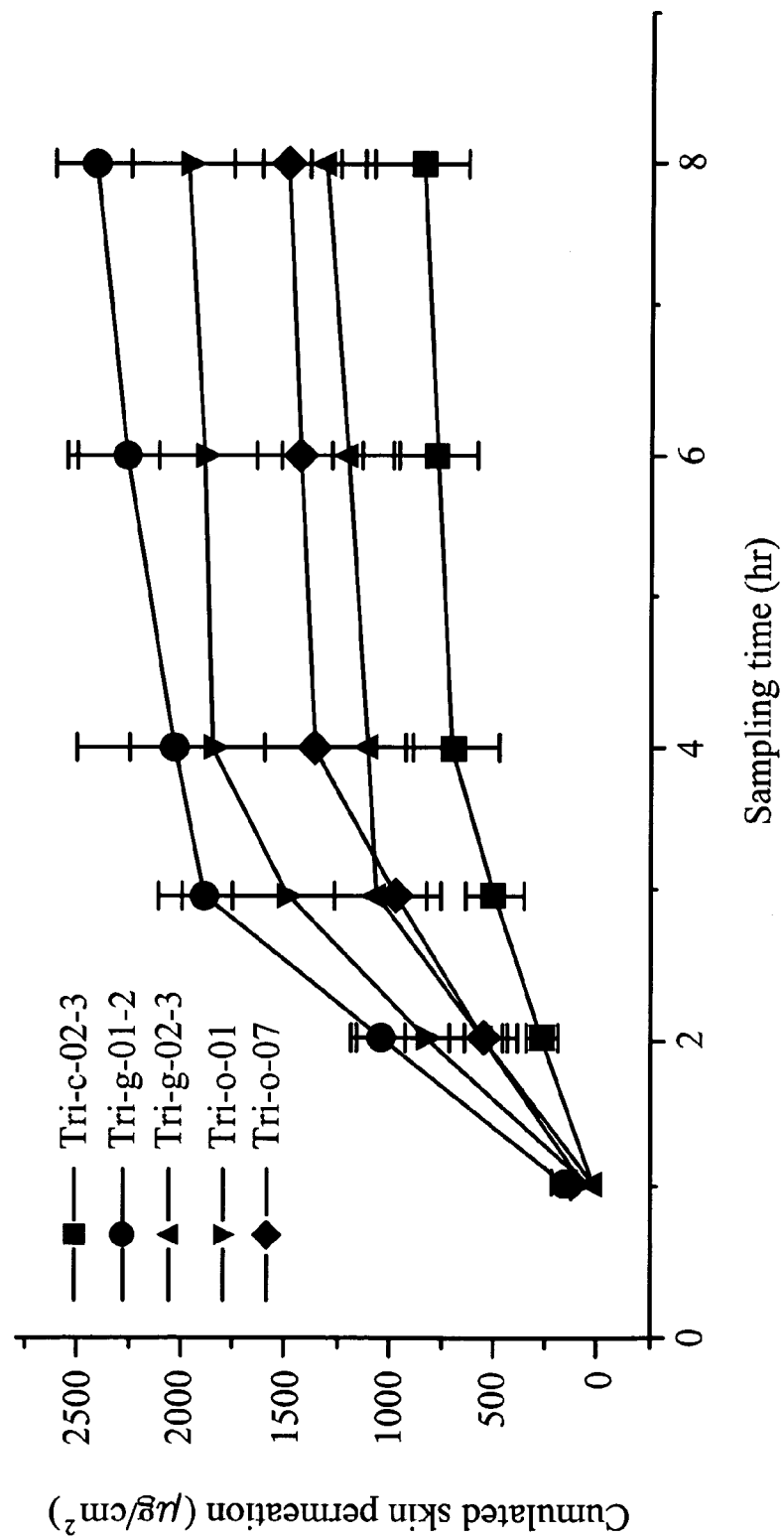
FIG. 1A shows pharmacokinetic studies of delivery of different PB formulations through the skin.

The skin, mucosa, or cornea providing a physical barrier to protect the body against infection and fluid loss is breached as a consequence of burn, trauma, inflammation, infection, neoplasia, or exposure to radiation or chemical agents. Injured keratinocytes are a source of growth factors (IGF, TGF-$\beta$1, TGF-$\beta$2, TGF-$\alpha$, PDGF, KGF) that initiate wound healing cascade by activating macrophages and recruiting inflammatory leukocytes that subsequently release cytokines/growth factors (IL-1, GM-CSF, TNF-$\alpha$, basic FGF, VEGF) for further chemo-attraction and new blood vessel and granulation tissue formation. Then activated fibroblasts release ground substance in dermal matrix to trigger epithelial cell to grow over it. Some activated fibroblasts differentiate into myofibroblasts that closure the wound more rapidly and deposit collagen matrix for tissue remodeling. When complete repair is achieved in a normal wound healing process, a feedback mechanism should occur to down-regulate the humoral and cellular activation. However, many conditions associated with abnormal wound healing are found. Diabetic ulcers are an example of impaired healing due to impaired granulocytic function and chemotaxis. On the other hand, keloids and hypertrophic scars are examples of fibroproliferative wound healing disorders due to increased activity of and exaggerated response to fibrogenic cytokines/growth factors (TGF-$\beta$1, TGF-$\beta$2, IGF, IL-1). In addition, abnormal epidermal-mesenchymal or dermal interactions and dysregulation in genes about cell growth control have also been linked to abnormal wound healing. That is, accelerated wound healing requires up-regulation of expression of growth factors in the early phase but prevention of scar formation requires down-regulation of expression of growth factor in the later phase, and abnormal wound healing could be a genetic disorder in cell growth control during the wound healing process.

A class compound of gene modulators, histone deacetylase (HDAC) inhibitors, activates and represses a subset of genes by remodeling the chromatin structure via the altered status in histone acetylation (Marks et al, J. Natl. Cancer Inst., 92: 1210-1216, 2000; Kramer et al, Trends Endocrinol. Metab., 12: 294-300, 2001). Histone hyperacetylation results in the up-regulation of cell-cycle inhibitors (p21Cip1, p27Kip1, and p16INK4), the down-regulation of oncogenes (Myc and Bcl-2), the repression of inflammatory cytokines (interleukin (IL)-1, IL-8, TNF-$\alpha$, and TGF-$\beta$), or no change (GAPDH and $\gamma$-actin) (Lagger et al, EMBO J., 21: 2672-2681, 2002; Richon et al, Clin. Cancer Res., 8: 662-667, 2002; Richon et al, Proc. Natl. Acad. Sci. USA., 97: 10014-10019, 2000; Van Lint et al, Gene Expr., 5: 245-243, 1996; Huang et al, Cytokine, 9: 27-36, 1997; Mishra et al, Proc. Natl. Acad. Sci. USA., 98: 2628-2633, 2001; Stockhammer et al, J. Neurosurg., 83: 672-681, 1995; Segain et al, Gut, 47: 397-403, 2000; Leoni et al, Proc. Natl. Acad. Sci. USA, 99:2995-3000, 2002). In addition to inducing histone hyperacetylation, HDAC inhibitors also induce hyperacetylation of non-histone proteins such as ribosomal S3, p53 or the Rel-A subunit of NF-$\kappa$B, modulate protein kinase C (PKC) activity, inhibit protein isoprenylation, decrease DNA methylation, and bind to nuclear receptors (Webb et al, J. Biol. Chem., 274: 14280-14287, 1999; Chen et al, Science, 293: 1653-1657, 2001). HDAC inhibitors have exhibited properties in inducing cell-cycle arrest, cell differentiation, and apoptotic cell death in tumor cells and in decreasing inflammation and fibrosis in inflammatory diseases (Warrell et al, J. Natl. Cancer Inst., 90: 1621-1625, 1998; Vigushin et al, Clin. Cancer Res., 7: 971-976, 2001; Saunders et al, Cancer Res., 59: 399-404, 1999; Gottlicher et al, EMBO J., 20: 6969-6978, 2001; Rombouts et al, Acta Gastroenterol. Belg., 64: 239-246, 2001). Although the effects of HDAC inhibitors induce bulk histone acetylation, they result in apoptotic cell death, terminal differentiation, and growth arrest in tumor cells but no toxicity in normal cells (Garber et al, J. Natl. Cancer Inst., 94: 793-795, 2002).

Thus, on the basis of the abilities in coordinately, selectively, differentially and epigenetically modulating the expression of cell growth control genes, proinflammatory cytokines (IL-1, TNF-$\alpha$), and fibrogenic growth factors (TGF-$\beta$1, 2), a pharmaceutical composition comprising the HDAC inhibitor may provide an effective treatment not only to accelerate wound healing but also to prevent scar formation.

Active compounds used to carry out the present invention are, in general, histone hyperacetylating agents, such as histone deacetylase inhibitors. Numerous such compounds are known. See, e.g., P. Dulski, Histone Deacetylase as Target for Antiprotozoal Agents, PCT Application WO 97/11366 (Mar. 27, 1997). Examples of such compounds include, but are not limited to:

A. Trichostatin A and its analogues such as: trichostatin A (TSA); and trichostatin C (Koghe et al. 1998. Biochem. Pharmacol. 56:1359-1364) (Trichostatin B has been isolated but not shown to be an HDAC inhibitor).

B. Peptides, such as: oxamflatin [(2E)-5-[3-[(phenylsufonyl) amino phenyl]-pent-2-en-4-ynohydroxamic acid (Kim et al. Oncogene, 18:2461-2470 (1999)); trapoxin A (TPX)—Cyclic Tetrapeptide (cyclo-(L-phenylalanyl-L-phenylalanyl-D-pipecolinyl-L-2-amino-8-oxo-9,10-epoxy-decanoyl)) (Kijima et al., J. Biol. Chem. 268, 22429-22435 (1993)); FR901228, depsipeptide (Nakajima et al., Ex. Cell Res. 241, 126-133 (1998)); FR225497, cyclic tetrapeptide (H. Mori et al., PCT Application WO 00/08048 (Feb. 17, 2000)); apicidin, cyclic tetrapeptide [cyclo(N—O-methyl-L-tryptophanyl-L-isoleucinyl-D-pipecolinyl-L-2-amino-8-oxode-canoyl)-] (Darkin-Rattray et al., Proc. Natl. Acad. Sci. USA 93, 13143-13147 (1996)); apicidin 1a, apicidin Ib, apicidin Ic, apicidin IIa, and apicidin IIb (P. Dulski et al., PCT Application WO 97/11366); HC-Toxin, cyclic tetrapeptide (Bosch et al., Plant Cell 7, 1941-1950 (1995)); WF27082, cyclic tetrapeptide (PCT Application WO 98/48825); and chlamydocin (Bosch et al., supra).

C. Hydroxamic acid-based hybrid polar compounds (HPCs), such as: salicylihydroxamic acid (SBHA) (Andrews et al., International J. Parasitology 30, 761-768 (2000)); suberoylanilide hydroxamic acid (SAHA) (Richon et al., Proc. Natl. Acad. Sci. USA 95, 3003-3007 (1998)); azelaic bishydroxamic acid (ABHA) (Andrews et al., supra); azelaic-1-hydroxamate-9-anilide (AAHA) (Qiu et al., Mol. Biol. Cell 11, 2069-2083 (2000)); M-carboxycinnamic acid bishydroxamide (CBHA) (Ricon et al., supra); 6-(3-chlorophenylureido) carpoic hydroxamic acid (3-Cl-UCHA) (Richon et al., supra); MW2796 (Andrews et al., supra); and MW2996 (Andrews et al., supra). Note that analogs not effective as HDAC Inhibitors are: hexamethylene bisacetamide (HBMA) (Richon et al. 1998, PNAS, 95:3003-3007); and diethyl bis (pentamethylene-N,N-dimethylcarboxamide) malonate (EMBA) (Richon et al. 1998, PNAS, 95:3003-3007).

D. Short chain fatty acid (SCFA) compounds, such as: sodium butyrate (Cousens et al., J. Biol. Chem. 254, 1716-1723 (1979)); isovalerate (McBain et al., Biochem. Pharm. 53:1357-1368 (1997)); valproic acid; valerate (McBain et al., supra); 4-phenylbutyrate (4-PBA) (Lea and Tulsyan, Anticancer Research, 15, 879-873 (1995)); phenylbutyrate (PB) (Wang et al., Cancer Research, 59, 2766-2799 (1999)); propionate (McBain et al., supra); butrymide (Lea and Tulsyan, supra); isobutyramide (Lea and Tulsyan, supra); phenylacetate (Lea and Tulsyan, supra); 3-bromopropionate (Lea and Tulsyan, supra); and tributyrin (Guan et al., Cancer Research, 60, 749-755 (2000)).

E. Benzamide derivatives, such as: MS-27-275 [N-(2-aminophenyl)-4-[N-(pyridin-3-yl-methoxycarbonyl) aminomethyl]benzamide] (Saito et al., Proc. Natl. Acad. Sci. USA 96, 4592-4597 (1999)); and 3'-amino derivative of MS-27-275 (Saito et al., supra).

F. Other inhibitors, such as: depudecin [its analogues (mono-MTM-depudecin and depudecin-bisether) do not inhibit HDAC] (Kwon et al. 1998. PNAS 95:3356-3361); and scriptaid (Su et al. 2000 Cancer Research, 60:3137-3142).

The description in this application is in particular directed to valproic acid, trichostatin A, and phenylbutyrate for promoting wound healing and decreasing fibrosis in the wounds, are offered as non-limiting examples and are not intended to limit the scope of the invention. Pharmaceutical formulations and the use of compounds of valproic acid, trichostatin A and phenylbutyrate are also disclosed.

In the course of the experiments, valproic acid, trichostatin A and phenylbutyrate as histone deacetylase inhibitors were discovered to have strong effects on not only accelerating wound healing but also preventing fibrosis in wounds due to radiation-induced injury, mechanical trauma, or infection in the skin or mucosa.

The histone deacetylase inhibitor agents can be brought in the form of pharmaceutically acceptable salts. As such pharmaceutically acceptable salts may be used so long as they do not adversely affect the desired pharmacological effects of the compounds. The selection and production can be performed by those skilled in the art. Examples of pharmaceutically acceptable salts include alkali metal salts such as a sodium salt or a potassium salt, alkaline earth metal salts such as a calcium salt or a magnesium salt, salts with an organic base such as an ammonium salt, or a salt with an organic base such as a triethylamine salt or an ethanolamine salt.

The histone deacetylase inhibitor agents of the present invention may be administered orally or non-orally. In the case of oral administration, they may be administered in the form of soft and hard micro or nano-capsules, tablets, granules, powders, solutions, suspensions, mouthwash or the like. In the case of non-oral administration, they may be administered in the form of creams, ointments, gels, lotions, patches, suppositories, liposome formations, injection solution, drip infusion formulations, enemas, eardrops, eyedrops or the like whereby continued membrane absorption can be maintained in the form of solid, viscous liquid, or suspension. The selection of the method for the preparation of these formulations and the vehicles, disintegrators or suspending agents, can be readily made by those skilled in the art. For example, the topical formulation includes, but is not limited to, a collagen-based cream, a collagen-based film, a collagen-based microcapsule, a collagen-based nanocapsule, a collagen-based liposome, a collagen-based powder, a collagen-based mesh, a hyaluronic acid or other glycosaminoglycan-based cream, a hyaluronic acid or other glycosaminoglycan-based foam, a hyaluronic acid or other glycosaminoglycan-based mesh, a hyaluronic acid or other glycosaminoglycan-based liposome, a hyaluronic acid or other glycosaminoglycan-based microcapsule, a hyaluronic acid or other glycosaminoglycan-based nanocapsule, a suture material, an epidermal skin substitute, a dermal skin substitute, a combined dermal and epidermal skin substitute, an artificial skin graft, a nylon mesh, or a wound dressing.

The composition of the present invention may further contain a cytokine, an interleukin, a growth factor, an angiogenic agent, an anti-neoplastic agent, an anti-inflammatory agent, an analgesic agent, an antipruritic agent, an antibacterial agent, an antiviral agent, an antifungal agent, an antiparasitic agent, an anti-oxidant agent, retinoic acid, an anti-fibrogenic agent, a vasoactive agent, an adenosine receptor agonist, or a peroxisome proliferating activator receptor (PPAR) agonist, in addition to valproic acid, trichostatin A, or phenylbutyrate, or other hyperacetylating agents or a pharmaceutically acceptable salt thereof and a pharmaceutically acceptable carrier. The growth factor can be epidermal growth factor (EGF), fibroblast growth factor (FGF), keratinocyte growth factor (KGF), transforming growth factor-alpha (TGF-α), transforming growth factor-beta (TGF-β), platelet-derived growth factor (PDGF), vascular endothelial growth factor (VEGF), insulin-like growth factor (IGF), or granulocyte macrophage-colony stimulating factor (GM-CSF). The cytokine can be interleukine-1, tumor necrosis factor-alpha (TNF-α), or interleukine-6. The angiogenic agent can be VEGF, TGF-β, basic FGF, angiogenin, angiopoietin 1, or thrombospondin. The anti-oxidant agent can be vitamin C, vitamin E, or superoxide dismutase. The anti-inflammatory agent can be corticosteroids, nonsteroidal anti-inflammatory drugs (NSAIDs), cyclosporine, colchicines, D-penicillamine, or TNF-α antagonists. The anti-fibrogenic agent can be interferons, TGF-β antagonists, or angiotensin-converting enzyme inhibitors. The antiviral agent can be Ganciclovir, Acyclovir, or Famciclovir.

As recognized by those skilled in the art, the effective doses vary depending on route of administration, excipient usage, and the possibility of co-use with other therapeutic treatments such as the use of a cytokine, an interleukin, a growth factor, an angiogenic agent, an anti-neoplastic agent, an anti-inflammatory agent, an analgesic agent, an antipruritic agent, an antibacterial agent, an antiviral agent, an antifungal agent, an antiparasitic agent, an anti-oxidant agent, retinoic acid, an anti-fibrogenic agent, a vasoactive agent, an adenosine receptor agonist, or a peroxisome proliferating activator receptor (PPAR) agonist. Effective amounts and treatment regimens for any particular subject (e.g., human, dog, or cat) will also depend upon a variety of other factors, including the activity of the specific compound employed, age, body weight, general health status, sex, diet, time of administration, rate of excretion, severity and course of the disease, and the patient's disposition to the disease, but are usually from 0.0001% to 100% by weight of the composition irrespective of the manner of administration. Active compounds of the present invention may optionally be administered in conjunction with other compounds useful in promoting wound healing and preventing scar formation. The other compounds may optionally be administered concurrently. As used herein, the word "concurrently" means sufficiently close in time to produce a combined effect (that is, concurrently may be simultaneously, or it may be two or more events occurring within a short time period before or after each other). As used herein, the administration of two or more compounds "concurrently" or "in combination" means that the two compounds are administered closely enough in time that the presence of one alters the biological effects of the other. The two compounds may be administered simultaneously or sequentially. Simultaneous administration may be carried out by mixing the compounds prior to administration, or by administering the compounds at the same point in time but at different anatomic sites or using different routes of administration.

As used herein, a wound comprises a burn, ischemic ulcer, decubitus ulcer, diabetic ulcer, surgical incision, laceration, ulcer resulting from a mechanical trauma, ulcer resulting from a chemical injury, ulcer resulting from a thermal damage, ulcer resulting from ionizing radiation, ulcer from an infectious process, ulcer resulting from an inflammatory process, ulcer resulting from an immune reaction, and ulcer resulting from a neoplastic process.

In order that the invention described herein may be more readily understood, the following examples are set forth. It should be understood that these examples are for illustrative purposes only and are not to be construed as limiting this invention in any manner. All references cited herein are expressly incorporated by reference in their entirety.

EXAMPLE

Example 1

Various Topical Compositions-Oleaginous Ointment Cream, and Gel

A. Preparation of an Oleaginous Ointment of Phenylbutyrate:

470 g of white petrolatum (Riedel-de Haen), 25 g of paraffin wax 50/52 (local supplier), and 5 g of 4-phenylbutyrate (Merck) were mixed in a beaker and heated at 70° C. to form a paste. The paste was stirred at 400 rpm for 1 hour, and then cooled at room temperature.

B. Preparation of an Oleaginous Ointment of Phenylbutyrate:

65 g of white petrolatum (Riedel-de Haen), 15 g of cetyl alcohol (Riedel-de Haen), 260 g of soft paraffin (Merck), 155 g of liquid paraffin (Merck), and 5 g of 4-phenylbutyrate (Merck) were mixed in a beaker and heated at 70° C. to form a paste. The paste was stirred at 400 rpm for 1 hour, and then cooled at room temperature.

C. Preparation of Cream of Phenylbutyrate:

Part I: 70 g of Tefose 63®, 20 g of Superpolystate®, 10 g of Coster 5000®, 15 g of Myriyol 318®, 15 g of Coster 5088®, and 15 g of GMS SE® (all commercially available from a local supplier) were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), and 149.061 g of deionized water were mixed in a beaker and heated at 70° C.

Part II was slowly added into part I and continually stirred at 400 rpm for 5 minutes to form a mixture. 2% Stabileze QM® (prepared by dissolving 2 g of Stabileze QM® in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

D. Preparation of Gel of Phenylbutyrate:

Part I: 10 g of Stabileze QM® and 232.035 g of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 232.035 g of deionized water, and 20 g of 10% NaOH were mixed in a beaker and heated at 70° C.

Part II was slowly added into part I and continually stirred at 400 rpm for 20 minutes to form a mixture. The mixture was cooled at room temperature.

E. Preparation of Gel of Phenylbutyrate:

Part I: 10 g of Stabileze QM® and 380.561 g of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 83.5 g of 1,2-propandiol, and 20 g of 10% NaOH were mixed in a beaker and heated at 70° C.

The part II was slowly added into the part I and continually stirred at 400 rpm for 20 minutes to form a mixture. The mixture was cooled at room temperature.

F: Preparation of Sustained Release Formulations of Phenylbutyrate:

Two formulations were prepared according to the compositions listed in the Table 1.

TABLE 1

Compositions of two sustained release formulations

| Composition | No. of formulation ||
| --- | --- | --- |
|  | Tri-s-04 | Tri-s-05 |
| PF-127 ® (BASF Inc.)* | 2 | 4 |
| Sodium carboxy-methylcellulose* | 12 | 12 |
| Deionized water | 82.8523 | 80.8523 |
| Sodium 4-phenylbutyrate | 1.1477 | 1.1477 |
| 85% phosphoric acid | 2 | 2 |
| pH | 5.93 | 6.01 |

*PF-127 ® is the base of the compositions, and sodium carboxymethylcellulose is a thickening agent.

G: Preparation of Liposomal Formulation of Phenylbutyrate:

In this liposomal formulation, egg phosphatidylcholine (EPC) and cholesterol were used in equi- or different-molar concentrations as primary lipid components. Various liposomes located with 4-phenylbutyrate were obtained by varying the lipid:phenylbutyrate ratio. Liposomes were prepared by thin film hydration, sized by membrane extrusion, and physically evaluated.

H: Preparation of Ointment of Trichostatin A:

472.5 g of white petrolatum (Riedel-de Haen), 27 g of paraffin wax 50/52 (local supplier), and 0.5 g of trichostatin A (sigma) were mixed in a beaker and heated at 70° C. to form a paste. The paste was stirred at 400 rpm for 1 hour, and then cooled at room temperature.

I. Preparation of an Oleaginous Ointment of Trichostatin A:

67.5 g of white petrolatum (Riedel-de Haen), 16 g of cetyl alcohol (Riedel-de Haen), 260.5 g of soft paraffin (Merck), 155.5 g of liquid paraffin (Merck), and 0.5 g of trichostatin A (sigma) were mixed in a beaker and heated at 70° C. to form a paste. The paste was stirred at 400 rpm for 1 hour, and then cooled at room temperature.

J. Preparation of Cream of Valproic Acid:

Part I: 70 g of Tefose 63®, 20 g of Superpolystate®, 10 g of Coster 5000®, 15 g of Myriyol 318®, 15 g of Coster 5088®, and 15 g of GMS SE® (all commercially available from local supplier) were mixed in a beaker and heated at 70° C.

Part II: 5.739 g of valproic acid (sigma), 0.125 g of methylparaben (Merck), 0.075 g of propylparaben (Merck), and 149.061 g of deionized water were mixed in a beaker and heated at 70° C.

The part II was slowly added into the part I and continually stirred at 400 rpm for 5 minutes to form a mixture. 2% Stabileze QM®D (prepared by dissolving 2 g of Stabileze QM® in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

Example 2

Topical Phenylbutyrate (Pb) Treatment Induces Histone Hyperacetylation in vivo

As shown in Table 2, several phenylbutyrate (PB) formulations were characterized.

TABLE 2

Formulation characteristics and pharmacokinetics parameters

| *PB (1%) Formulation | Tri-c-02-3 | Tri-g-01-2 | Tri-g-02-3 | Tri-o-01 | Tri-o-07 |
|---|---|---|---|---|---|
| Stability | Good | good | good | good | Poor |
| Shelf-life(mo) | 83.9 | 10.8 | 23.9 | 2.0 | 6.1 |
| Skin irritation | No | No | No | No | No |
| 1Slope | 219.9 | 873.5 | 491.7 | 709.25 | 452.8 |
| 2Y Intercept | −198.3 | −740.7 | −442 | −649.4 | −400.7 |
| 3Retention time | 0.902 | 0.848 | 0.899 | 0.916 | 0.885 |
| 4Constant | 1.18 | 1.26 | 1.19 | 1.16 | 1.21 |
| 5Cs | 1.49 | 5.56 | 3.32 | 4.87 | 3.01 |
| 6 µg/cm2 | 594.8 | 2222.2 | 1326.1 | 1948.2 | 1202.1 |
| 7 mg/cm3 | 74 | 278 | 166 | 243 | 150 |

*c: cream; g: gel; o: ointment;
1slope, indicating the permeation amount of each drug through skin per hour (µg/cm2/hr);
2Y intercept (µg/cm2): a negative number indicating the potential permeation amount of each drug through skin, a positive number indicating that the sampling time is too long to obtain an accurate value;
3retention time, indicating the average time (hr) that drug spends to permeate skin;
4Constant (×10−5 cm2/s), the drug diffusion constant;
5Cs (×105 mg/cm3), the drug concentration on skin surface;
6 µg/cm2, the average permeation amount of each drug through per cm2 skin;
7 mg/cm3, the average concentration in skin.

Figure 1B:
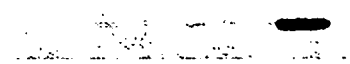
FIG. 1B shows western blot analysis for acetylated H3 in the irradiated skin (40 Gy single fraction) treated with or without phenylbutyrate cream (PB) for 6 hours after irradiation. 1, Normal skin without irradiation; 2, irradiated skin without any treatment; 3, irradiated skin treated with the vehicle; 4, irradiated skin treated with the 1% PB cream.
Figure 1B:
Figure 1C:
FIGS. 1C-1F show immunofluorescence staining of acetylated H3 in the irradiated skin treated with or without the phenylbutyrate cream (PB) for 6 hours after irradiation.
Figure 1D:
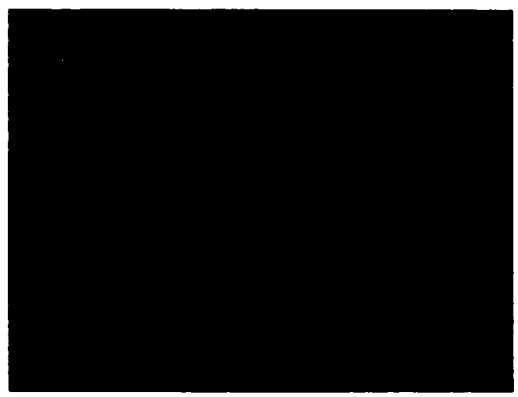
Figure 1E:
Figure 1F:

Among the different formulations, the PB cream (Tri-c-02-3), which showed good stability, low rates of skin irritation, a long shelf life, and a high rate of skin penetration, was selected for testing (FIG. 1A). To determine what dosage of topical PB was suitable to treat irradiated skin, the amount of histone hyperacetylation in the nucleus was used as a marker to demonstrate the extent of drug penetration and to indicate whether the local drug concentration was sufficient to exert biological effects. Western blot analysis for acetylated histones in the irradiated skin 6 hours after irradiation (40 Gy single fraction) showed that the acetylated form of histone H3 was mildly increased in the control and vehicle-treated groups but was markedly increased with the topical treatment of 1% PB cream at a dose of 200 mg/irradiated skin surface given immediately after irradiation (FIG. 1B). The coomassie blue-stained gel sections demonstrate the equivalence of protein loading. Immunofluorescence staining further demonstrated that histone hyperacetylation in irradiated skin was visually evident deep in the subcutaneous layer at 6 hours after drug treatment (i.e., coincident with the peak of the drug concentration in the skin test) (FIGS. 1A, and 1C-1F). The acetylated H3 in the nuclei was used as a marker indicating the extent of drug penetration.

Example 3

Histone Deacetylase Inhibitors are Effective for Reducing Acute Radiation-Induced Normal Tissue Damage Adult female Sprague Dawley (SD) rats were purchased from the animal center of the National Science Council of Taiwan, and weighed 250-300 g at the time of irradiation. Each rat was caged alone and allowed chow and water. They were anesthetized with pentobarbital 50 mg/kg i.p. before irradiation. The skin over the gluteal area was shaved completely and radiation fields with 2-cm diameter were outlined with a marking pen just prior to irradiation. An electron beam with 6 MeV energy produced by a linear accelerator was used. The dose was delivered on Day 0 at 4 Gy/min up to 40 Gy to the prepared area. Each group treated with a histone deacetylase inhibitor was further divided into three subgroups animals (5 each): one subgroup treated with skin irradiation followed by vehicle, another with skin irradiation followed by a histone deacetylase inhibitor, and the third with skin irradiation only. Then vaseline (negative control), madecassol ointment (positive control), or either vehicles or the 1% phenylbutyrate cream, 1% valproic acid cream, or 0.1% trichostatin A ointment were applied topically to the irradiated skin twice daily from Day 1 to Day 90 after irradiation. The mean dosage for each treatment in the respective groups was 16 mg vaseline per cm2 skin, 16 mg madecassol per cm2 skin, 50 mg phenylbutyrate per cm2 skin, 50 mg valproic acid per cm2 skin, 5 mg trichostatin A per cm2 skin, and an equivalent amount of the vehicle base for the control groups. The gross skin reactions were evaluated in all rats. Acute skin reactions were evaluated and scored every other day until the 90th day after irradiation using the modified skin score system (Abe Y. and Urano M. Fraction size-dependent acute skin reaction of mice after multiple twice-a-day doses. International Journal of Radiation Oncology, Biology, Physics. 18(2):359-64, 1990): 0=normal, 0.5=slight epilation, 1.0=epilation in about 50% of the radiated area, 1.5=epilation in greater than 50% of the area, 2.0=complete epilation, 2.5=complete epilation with definitive edema or dry desquamation in more than 50% of the area, 3.0=moist desquamation in a small area, 3.5=moist desquamation in most of the area.

Figure 2:
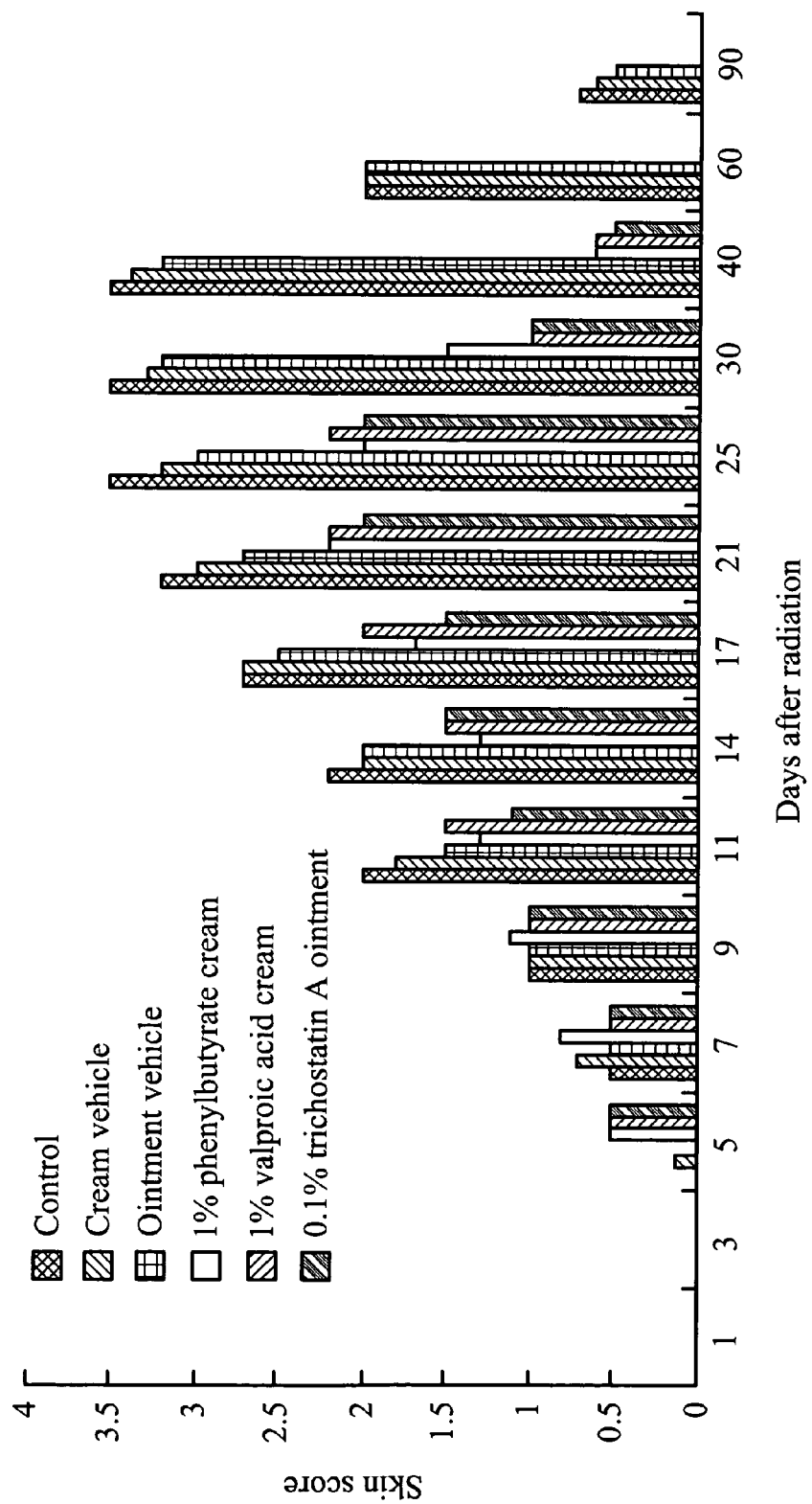
FIG. 2 is an acute skin reaction score diagram showing the time-course of the average skin score after 40 Gy irradiation.
Figure 3C:
Figure 3B:
Figure 3A:
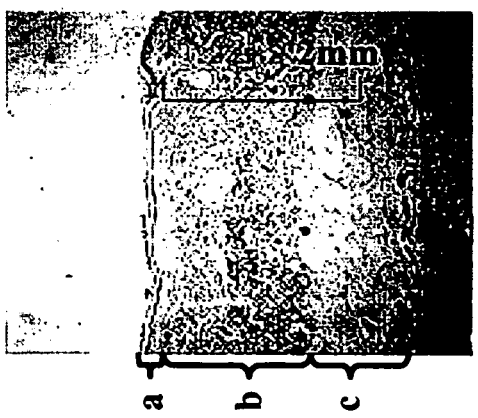
Figure 3I:
Figure 3H:
Figure 3G:
Figure 4A:
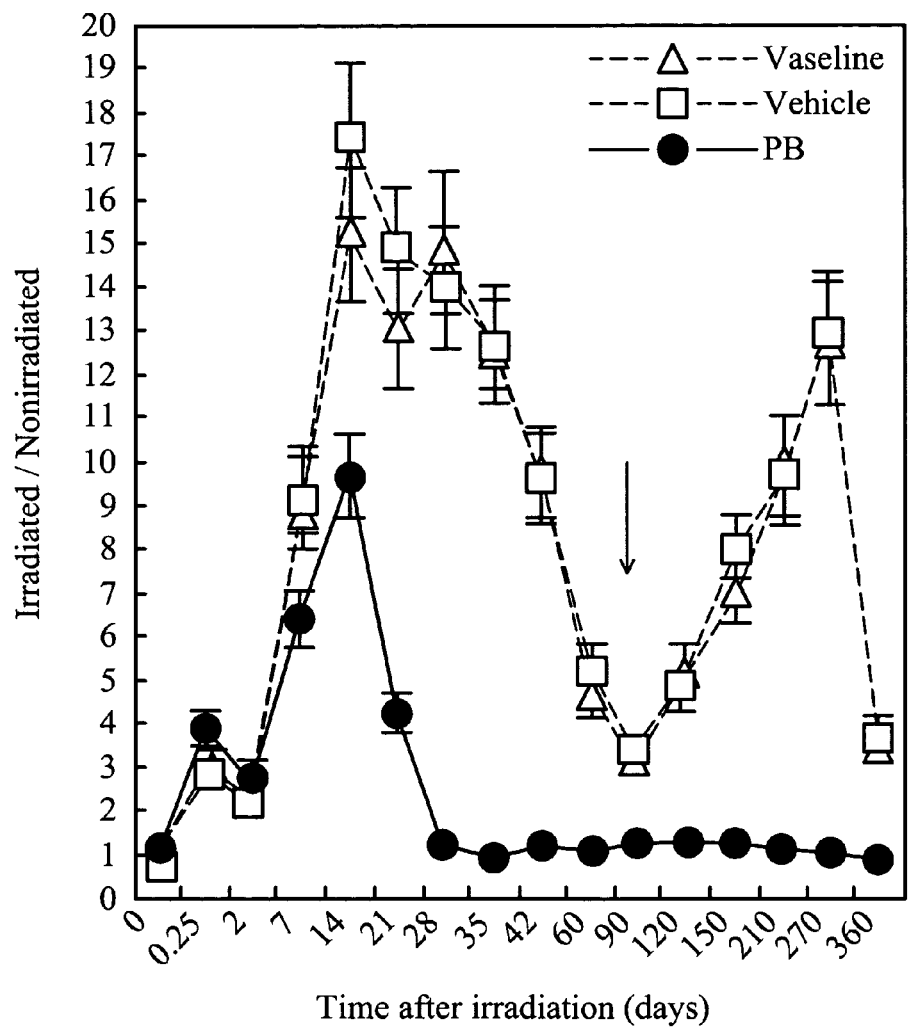
FIGS. 4A-4D shows the expression levels of TGF-$\beta$ and TNF-$\alpha$ after irradiation treated with or without the topical HDAC inhibitor. Temporal variation in mRNA levels of TGF-$\beta$1, TGF-$\beta$2, TGF-$\beta$3, and TNF-$\alpha$ in skin after irradiation is normalized to the internal control GAPDH and expressed as a ratio to levels in nonirradiated control samples. Each point represents the mean of mRNA levels of 5 samples in the same group of Vaseline, vehicle, or phenylbutyrate (PB). The arrow indicates that the drug treatment was discontinued after Day 90 ($*p<0.05$, $**p<0.001$ in comparison with the PB-treated and vehicle groups).
Figure 4B:
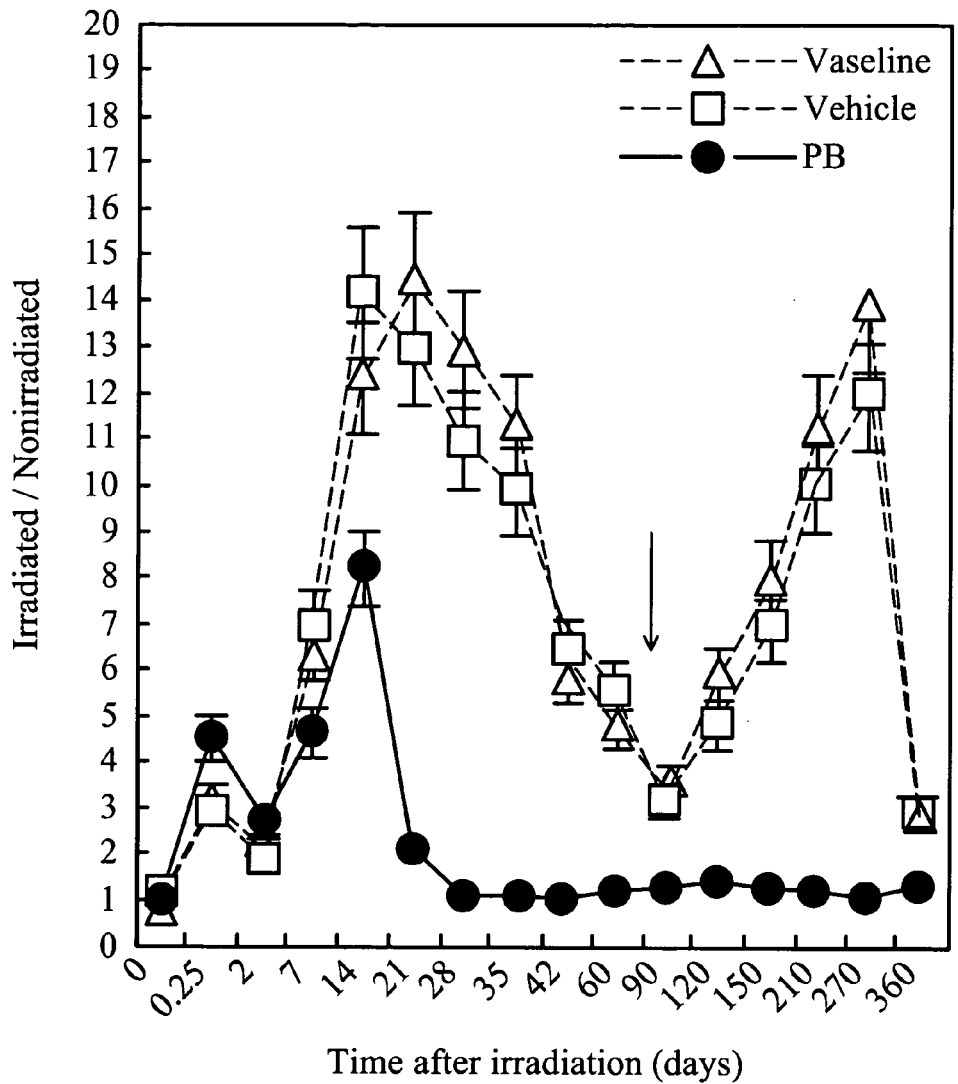
Figure 4C:
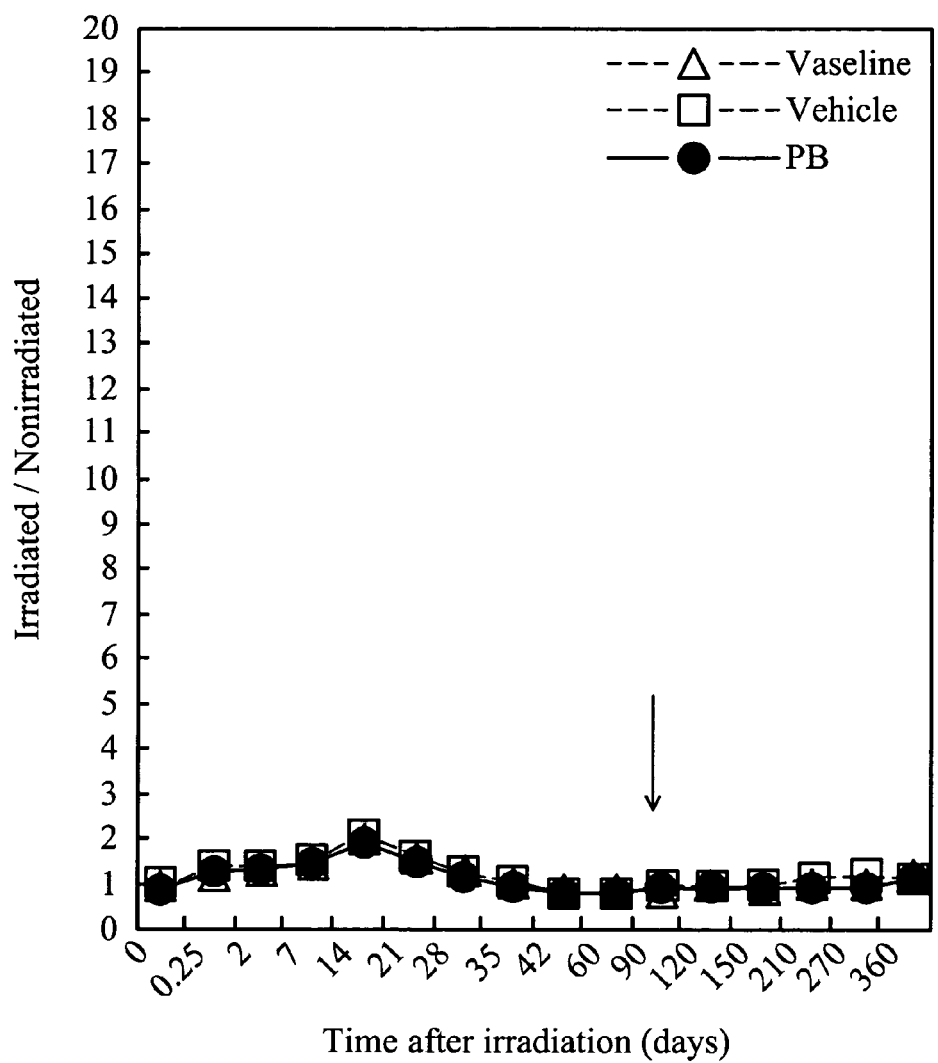
Figure 4D:
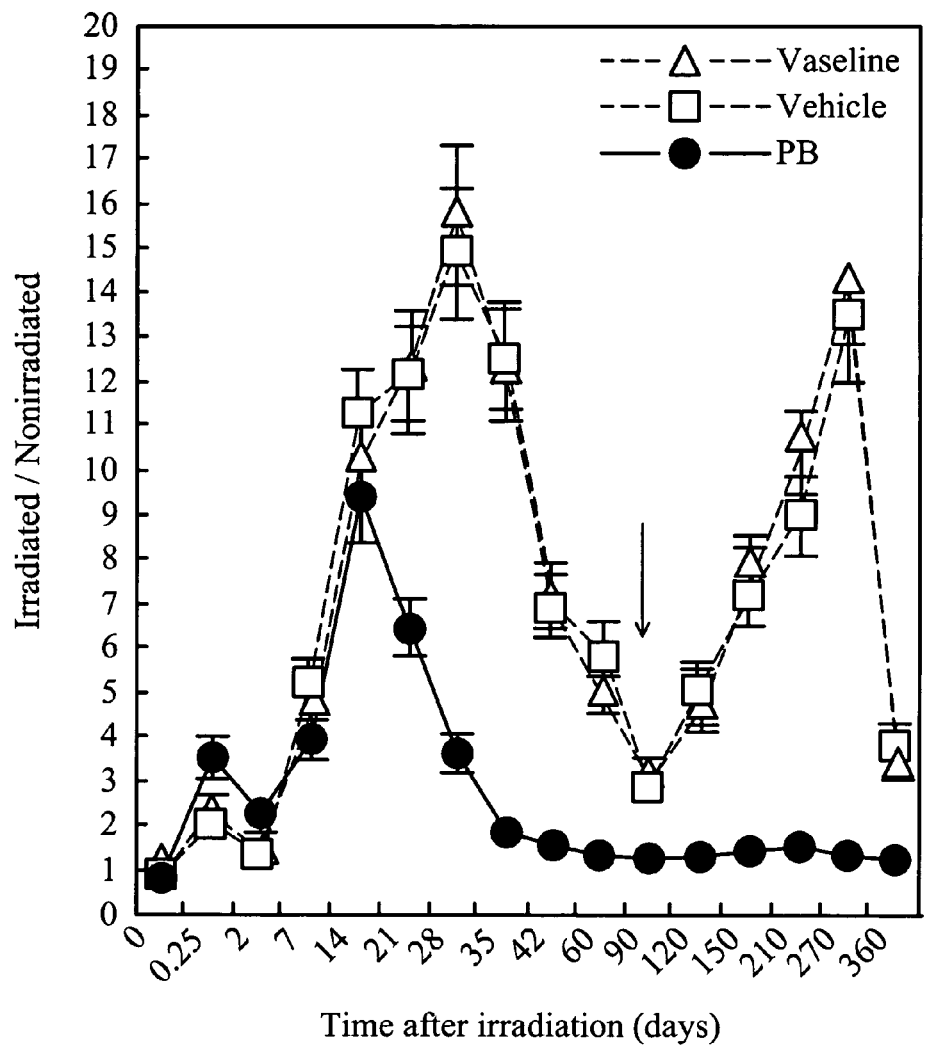
Figures 5A, 5B, 5C, 5D:
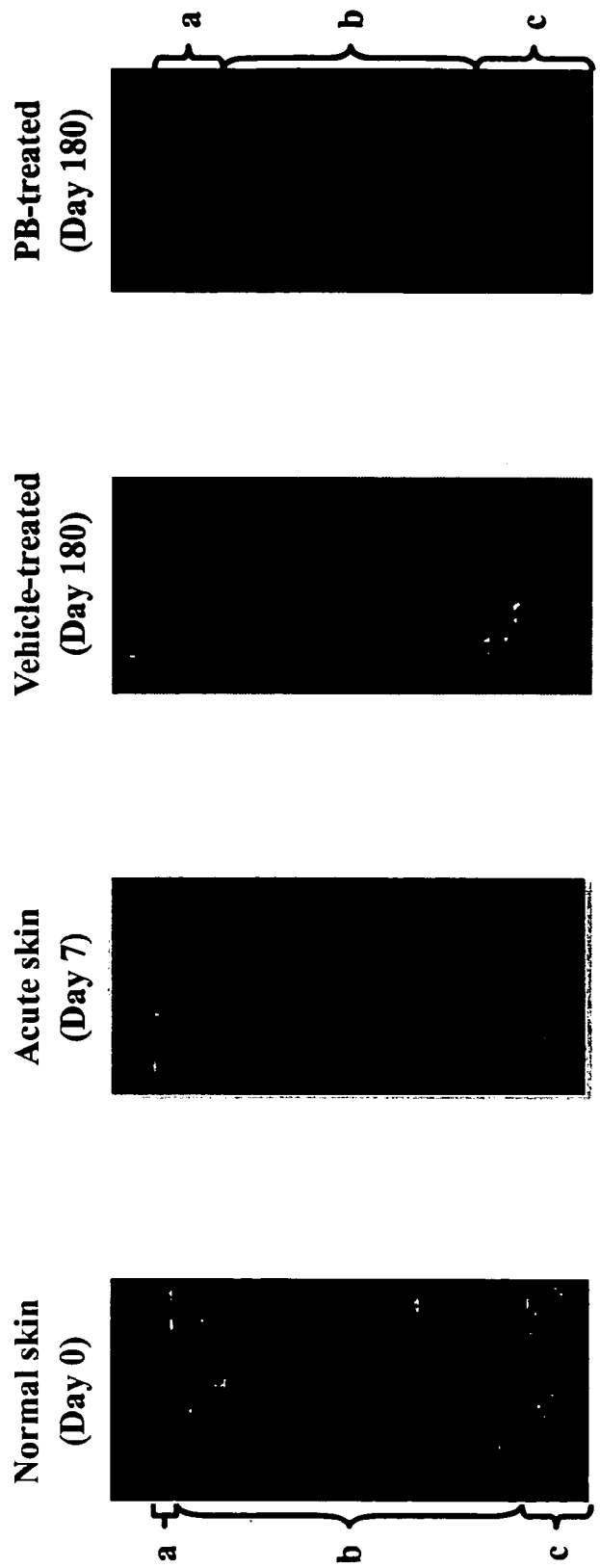
FIGS. 5A-5D are photographs of immunofluorescence with the anti-TGF-beta 1, 2 antibodies showing that the expression of TGF-beta, a fibrogenic growth factor, was suppressed by the histone deacetylase inhibitor in example 4.
Figure 6A:
FIGS. 6A-6D are photographs of immunohistochemistry with the anti-TNF-$\alpha$ antibody showing that the expression of TNF-$\alpha$, a proinflammatory cytokine, was suppressed by the histone deacetylase inhibitor.
Figure 6B:
Figure 6C:
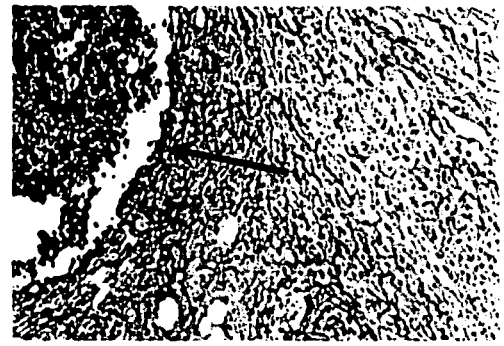
Figure 6D:
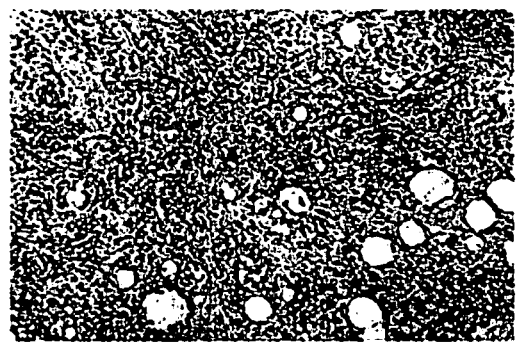

The skin score increases with more severe skin reaction. The average skin reaction scores in each group are shown in FIG. 2. On Day 11, the skin reactions in the groups treated with madecassol (positive control) or histone deacetylase inhibitors were less marked than those in the negative or vehicle control groups. By day 21, the epilation in the negative or vehicle groups had progressed to wet desquamation in most areas whereas in the madecassol or histone deacetylase inhibitor groups, it improved, and epithelium healing had begun quickly.

Example 4

H&E Histology of Irradiated Skin Correlates with Promotion of Wound Healing and Prevention of Scar Formation by the HDAC Inhibitor Valproic acid, trichostatin A, and phenylbutyrate are structurally unrelated histone deacetylase inhibitors, and all have similar effects on suppressing the radiation-induced skin damage including acute dermatitis and desquamation, and late fibrosis, ulceration and necrosis. As shown in FIG. 3, the groups treated with histone deacetylase inhibitors for 180 days have thicker epidermis with more cell layers but have thinner dermis (measured from epidermis to the subcutaneous fat layer) with less collagen deposition when compared to the vehicle group on Day 180 and the control groups (normal skin and acute reaction on Day 7).

Example 5

Changes in Radiation-Induced Histology After Treatment with the HDAC Inhibitor Correlate with Up-Regulation of Inflammatory and Fibrogenic Cytokine Expressions in the Early Wound Healing Phase but Suppression in the Later Phase Because the development of radiation-induced damage has been attributed to radiation-induced temporal changes and the persistent up-regulation of proinflammatory cytokines such as TNF-$\alpha$ and fibrogenic growth factors such as TGF-$\beta$1 and $\beta$2, the suppression of radiation-induced damage by the HDAC inhibitor is shown to correlate with the suppression of TNF-$\alpha$ and TGF-$\beta$ expression.

The timing of the peak appearance of TGF-$\beta$1, TGF-$\beta$2, and TNF-$\alpha$ expression levels induced by radiation correlated with the beginning of development of radiation-induced damage (FIG. 4). Levels of TGF-$\beta$1, TGF-$\beta$2, TGF-$\beta$3, and TNF-$\alpha$ mRNA were assessed using a multiple cytokine RNase protection assay kit (Riboquant; Pharmingen, San Diego, Calif.) that contained a template set to allow for the generation of a 32P-labeled antisense RNA probe set that hybridized with the target mRNA for TGF-$\beta$1, TGF-$\beta$2, TGF-$\beta$3, TNF-$\alpha$, and internal control GAPDH. After hybridization of labeled probe to target RNA, unprotected RNA was digested by a ribonuclease (RNase), and protected RNA fragments were resolved on a 6% polyacrylamide gel and recorded by phosphorimaging (Molecular Dynamics Corp., Sunnyvale, Calif.). Densitometry was used to quantify the amount of each mRNA species and was normalized to the internal control GAPDH.

The means of skin scores for skin reactions from five rats in each group were calculated. The average levels of cytokine/growth factor mRNA from three skin samples in each group were normalized to the internal control GAPDH and expressed as a ratio to the average level in time-matched control groups. The Mann-Whitney test (Stata Statistical Software, College Station, Tex.) was used to determine statistical significance at the $p<0.05$ level for differences in average skin scores and in average mRNA levels, respectively, between treated and control rats.

In the phenylbutyrate (PB)-treated group, the highest surge of TGF-$\beta$1, TGF-$\beta$2, and TNF-$\alpha$ appeared at 6 hours after irradiation, but levels were subsequently suppressed after Day 14. The suppression still persisted at 12 months, even when topical PB treatment was discontinued at Day 90. In the Vaseline and vehicle control groups, mRNA levels of TGF-$\beta$1, TGF-$\beta$2, and TNF-$\alpha$ in the irradiated skin increased and fluctuated above the non-irradiated control levels over a period of 1 year and reached the first peak of 2-3-fold above the non-irradiated control levels at 6 hours after irradiation, the second peak of 10.5-16-fold around 14-28 days after irradiation, and the third peak of 13-14-fold at 9 months after irradiation; levels then declined to 2-3-fold normal levels by 12 months after irradiation. Although the mRNA levels of TGF-$\beta$1, TGF-$\beta$2, and TNF-$\alpha$ at the first peak at 6 hours in the PB group were higher than those in the Vaseline and vehicle control groups, they decreased to levels lower than those in the Vaseline and vehicle groups at Day 14 and returned to the non-irradiated control levels at Day 28-35.

TGF-$\beta$1 and TGF-$\beta$2 have similar cellular effects in inhibiting epithelial cell growth and promoting dermal fibroblast proliferation, but TGF-$\beta$3 has the opposite effect. The level change of TGF-$\beta$3 mRNA was found to exhibit a slightly transient increase of 2-fold in all irradiated groups at 14 days then progressively decrease to the non-irradiated control level or lower. No significant differences in TGF-$\beta$3 mRNA levels were observed between the irradiated groups treated with Vaseline, vehicle, or PB.

Example 6

Immunofluorescence of TGF-beta, a Fibrogenic Growth Factor, is Suppressed in the Late Tissue Remodeling to Prevent Scar Formation by the Histone Deacetylase Inhibitor The same pathological sections in example 4 were subjected to immunofluorescence with the anti-TGF-beta1, 2 antibodies. As shown in FIGS. 5A-5D, the TGF-beta protein, a strong fibrogenic factor, was up-regulated by irradiation, and highly expressed in fibrogenic skin both in keratinocytes of the epidermis and in myofibroblasts of the dermis on Day 7 and Day 180 in the acute reaction and vehicle-treated group, respectively, but the expression of TGF-beta was suppressed effectively in the PB-treated group on Day 180 which showed less collagen deposit compared to the control groups.

Example 7

Immunohistochemistry of TNF-Alpha, a Proinflammatory Cytokine, is Suppressed in the Late Tissue Remodeling to Prevent Chronic Skin Ulceration by the Histone Deacetylase Inhibitor On Day 270, three of five rats in the Vaseline-treated group and four of five rats in the vehicle-treated group, compared with zero of five rats in the PB-treated group, showed chronic ulceration, necrosis, bullae formation, and inflammatory cell infiltration. The decrease in late radiation-induced skin damage by topical PB was consistent with the suppression of TNF-α expression (FIGS. 6A-6D).

Example 8

Figure 7:
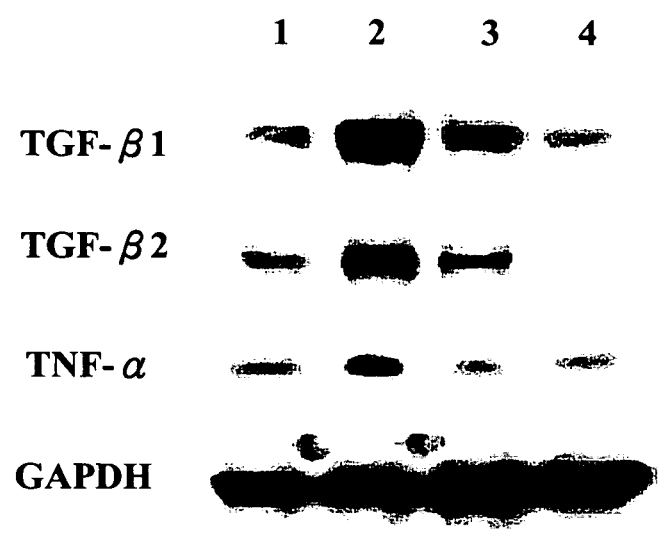
FIG. 7 is a northern blot assay showing that the up-regulation of TGF-$\beta$1, 2, and TNF-$\alpha$ expression in skin after irradiation is suppressed by structurally unrelated HDAC inhibitors (trichostatin A and valproic acid). 1, normal skin (Day 0); 2, acute reaction (Day 14); 3, valproic acid-treated (Day 14); and 4, trichostatin A treated (Day 14).

Similar Effects of Structurally Unrelated Antitumor HDAC Inhibitors in Promoting Radiation-Induced Wound Healing In addition to phenylbutyrate (PB), other structurally unrelated HDAC inhibitors, such as trichostatin A (an antifungal agent) and valproic acid (an anti-seizure agent), also ameliorated the development of radiation-induced skin wound and scar formation and decreased the radiation-induced TGF-β1, TGF-β2, and TNF-α over-expression (FIG. 7 and Table 3).

Total RNA was isolated from frozen skin samples using Trigent (Molecular Research Center Inc., Cincinnati, Ohio). Total RNA (30 μg) was electrophoresed in a denaturing formaldehyde-agarose gel, blotted onto Hybond N (Amersham, Amersham, UK), and fixed by ultraviolet (UV) irradiation. The membrane was incubated with 32P-labeled probes, as described below, in Rapid-hyb buffer (Amersham). To prepare probes for rat TGF-β1 and TGF-β2, their full-length coding sequences were amplified by reverse-transcription polymerase chain reaction using specific forward (TGF-β1, 5'-CGGGTGGCAGGCGAGAGC-3' (SEQ ID NO:1) and TGF-β2, 5'-CATGCACTACTGTGTGCT-3' (SEQ ID NO:2)) and reverse (TGF-β1, 5'-GGAATTGTTGC-TATATTTCTGC-3' (SEQ ID NO:3) and TGF-β2, 5'-CCGAGGACTTTAGCTGCA-3' (SEQ ID NO:4))primers. A template set of TNF-α and GAPDH from the RNase protection assay kit (Riboquant; Pharmingen) was used to generate 32P-labeled antisense RNA probes that hybridized with the mRNA for TNF-α and GAPDH.

TABLE 3

Summary of histological findings in promoting radiation-induced wound healing with different HDAC inhibitors

| Treatment group | Irradiated skin reaction | | | | | | | | |
|---|---|---|---|---|---|---|---|---|---|
| | Day 1–90 | | | Day 90–180 | | | Day 180–360 | | |
| | A | B | C | D | E | F | G | H | I |
| Vaseline | +++++ | +++++ | +++ | +++++ | | | +++++ | +++ | |
| Madecassol | +++++ | ++ | | +++++ | | + | ++++ | + | + |
| Cream vehicle | +++++ | +++++ | +++ | +++++ | | | +++++ | ++++ | |
| Ointment vehicle | +++++ | +++++ | +++ | +++++ | | | +++++ | +++ | |
| 1% phenylbutyrate cream | +++++ | ++ | | | +++++ | +++++ | | | +++++ |
| 1% valproic acid cream | +++++ | ++ | | | +++++ | +++++ | | | +++++ |
| 0.1% trichostatin A ointment | +++++ | ++ | | | +++++ | +++++ | | | +++++ |

The histological findings on skin specimens from 5 irradiated rats in each group are represented as follows: A, subepithelial swelling; B, dry desquamation in more than 50% of the area; C, wet desquamation in more than 50% of the area; D, atrophy of epidermis in most areas; E, atrophy of skin appendages in most areas; F, increased thickness of epithelium with more cell layers; G, increased collagen deposition, more vessel density, and increased thickness of dermis; H, chronic ulceration, necrosis, bullae formation, and more inflammatory cell infiltrate; I, down-regulation of TGF-β1, 2, and TNF-α. The "+" to "+++++" means specimens from one to five rats showed the reaction or effect as indicated.

Example 9

Animal Model of Treatment of Radiation-Induced Mucositis with Topical Phenylbutyrate Hamster models of chemotherapy-induced mucositis and radiation-induced mucositis have been developed. The reproducibility of the model has been validated, with the consistent appearance of ulcerative mucositis between days 12 and 15 following radiation. Using this model, the efficacies of topical phenylbutyrate gel and solution have been tested for their abilities to modify the course of radiation-induced mucositis. An acute radiation dose of 40 Gy on Day 0 was administered in order to produce severe mucositis around Day 15. The use of acute radiation to induce mucositis was preferable to the use of either fractionated radiation or chemotherapy for these initial studies. The acute model had little systemic toxicity, resulting in fewer animal deaths. This fact permitted the use of smaller groups in the initial studies. The acute model has been used successfully to demonstrate the presence or absence of efficacy for a large number of compounds. The acute radiation model is therefore appropriate as an initial protocol for screening diverse families of compounds.

Mucositis was induced using an acute radiation protocol. A single dose of radiation (40 Gy/dose) was administered to all animals on Day 0. Radiation was generated with a 250 kilovolt potential (15 mA) source at a focal distance of 50 cm, hardened with a 0.35 mm Cu filtration system. Irradiation targeted the left buccal pouch mucosa at a rate of 121.5 cGy/minute. Prior to irradiation, animals were anesthetized with an intraperitoneal injection of sodium pentobarbital (80 mg/kg). The left buccal pouch was everted, fixed, and isolated using a lead shield.

This study used twenty hamsters that were randomly divided into four groups of five animals per group. Each group was assigned a different treatment as follows: Group 1 animals: 20 μl PBS/hamster; Group 2 animals: 200 μg sodium phenylbutyrate/20 μl PBS/hamster; Group 3 animals: 20 mg placebo (gel base)/hamster; Group 4 animals: 20 mg phenylbutyrate gel/hamster. The substances were applied topically to the radiation-induced mucositis area of test hamsters once daily for 10 consecutive days since Day 15. The mucositis wound area, traced onto the clear plastic sheets on Day 15, 17, 19, 21, 23, and 25, was quantitated by use of an Image Analyzer (Life Science Resources VISTA, Version 30). The mucositis wound area half-closure time (CT50) was determined by linear regression using GraphPad Prism (Graph Pad Software USA) and unpaired Student's t test was applied for comparison between treated and placebo group at each measurement time point. Differences were considered statistically significant at p<0.05.

As shown in Table 4, significant increase (p<0.01) in mucositis wound closure was observed in Group 2 (200 μg sodium phenylbutyrate/20 μl PBS/hamster) on Day 21, 23 and 25, and in Group 4 (20 mg phenylbutyrate gel/hamster) on Day 17, 19, 21, 23 and 25. CT50 was also significantly reduced (p<0.01) to 6.5±0.2 days in Group 2 (relative to 7.7±0.2 days in Group 1), and to 8.9±0.2 days in Group 4 (relative to 10.5±1.3 days in Group 3).

TABLE 4 mucositis wound healing treated with phenylbutyrate (PB)

| Group (5 hamsters each) | Treatment (topically applied × 10 daily since Day 15 after radiation) | Averaged (N = 5) closure of mucositis wound (%) | | | | | CT50 Days |
|---|---|---|---|---|---|---|---|
| | | Day 17 | Day 19 | Day 21 | Day 23 | Day 25 | |
| 1. (Solution control) | 20 μl PBS/hamster | 24.0 ± 3.0 | 42.6 ± 1.2 | 49.6 ± 1.7 | 57.6 ± 1.8 | 65.0 ± 2.5 | 7.7 ± 0.2 |
| 2. (PB solution) | 200 μg sodium phenylbutyrate/ 20 μl PBS/hamster | 28.2 ± 4.3 | 45.8 ± 2.9 | 57.4 ± 1.2** | 69.2 ± 1.4** | 74.8 ± 1.5** | 6.5 ± 0.2** |
| 3. (Gel control) | 20 mg placebo (gel base)/hamster | 9.0 ± 5.6 | 14.8 ± 6.0 | 34.8 ± 5.5 | 47.8 ± 5.3 | 54.4 ± 7.7 | 10.5 ± 1.3 |
| 4. (1% PB gel) | 20 mg phenylbutyrate gel/hamster | 26.3 ± 3.8* | 33.6 ± 2.0** | 40.8 ± 2.8** | 50.8 ± 2.8** | 58.2 ± 2.5** | 8.9 ± 0.2** |

Differences are considered significant at *P < 0.05, **P < 0.01.

Example 10

Topical Phenylbutyrate (PB) Ameliorates the Skin Ulcer from Cutaneous Neoplasia

The syngeneic carcinoma cells 1MEA7R.1 (purchased from American Type Culture Collection, Manassas, Va.) were subcutaneously injected into the flank areas of female BALB/c mice. The tumor was allowed to grow to a maximum dimension of 0.5 cm. Topical HDAC inhibitors or vehicle was applied at a dose of 200 mg/mouse to cover the whole tumor surface and surrounding skin twice per day for 4 weeks.

Figure 8A:
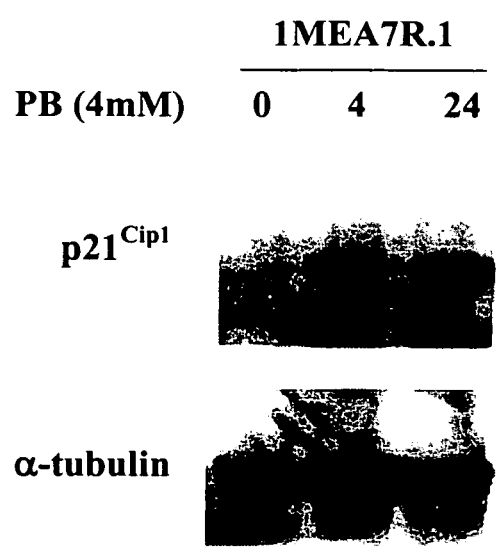
FIGS. 8A-8D show that the topical phenylbutyrate (PB) ameliorates the skin ulcer resulting from neoplasia.
Figure 8D:
Figure 8C:
Figure 8B:
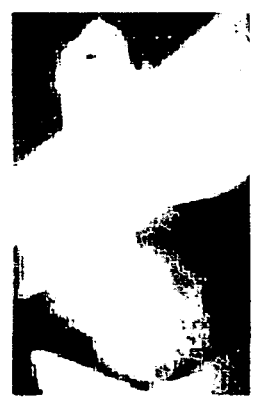

BNL 1MEA7R.1 carcinoma cells, which showed growth inhibition by PB in vitro by the up-regulation of p21Cip1, a cell-cycle inhibitor (FIG. 8A), were inoculated into the back of syngeneic mice. Cutaneous tumors were allowed to grow to the largest dimension 0.5 cm (FIG. 8B), and PB was topically applied to the tumor surface at 200 mg/mouse twice per day. By 4 weeks, the tumor sizes of 1MEA7R.1 carcinomas in the placebo groups were almost 6-fold larger than those in the PB-treated groups (FIGS. 8C-8D). Moreover, cutaneous tumors in the PB-treated groups grew slowly without skin ulceration (FIG. 8D), whereas tumors in the control or placebo group grew rapidly and showed a necrotic appearance and skin ulceration (FIG. 8C).

Example 11

Figure 9A:
FIGS. 9A-9B show that the topical trichostatin A (TSA) promotes the wound healing resulting from bacterial injection, inflammation and immune reaction.
Figure 9B:
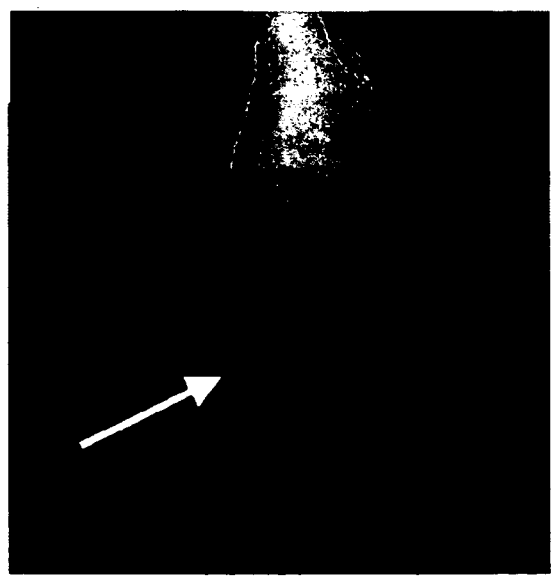

The HDAC Inhibitor Promotes the Ulcer Healing from Infection, Inflammation, and Immune Reaction Groups of 5 Long Evans rats weighing 150±20 g were used. A well-ground suspension of killed Mycobacterium tuberculosis (DIFCO, USA; 0.3 mg in 0.1 ml of light mineral oil; Complete Freund's Adjuvant, CFA) was administered into the subplantar region of the right hind paw. The skin wound was induced by the Mycobacterium tuberculosis injection into the sub-plantar region. The 1% of trichostatin A ointment at a dose of 200 mg/paw and 10 mg/paw, respectively, were applied topically twice daily for 18 consecutive days after bacterial injection. FIGS. 9A and 9B are back views of ankle and plantar joint. Healing is promoted in the plantar skin wound in the treated group using the HDAC inhibitor.

Example 12

Promotion of Abrasive Wound Healing by the HDAC Inhibitors

Groups of 5 ICR derived male mice weighing 22±2 g, provided by animal breeding center of MDS Pharma Service-Taiwan, Ltd., were used. Under hexobarbital (90 mg/kg, IP) anesthesia, the shoulder and back region of each animal was shaved. A sharp punch (ID 12 mm) was used to remove the skin including panniculus carnosus and adherent tissues. The wound area, traced onto the clear plastic sheets on day 3, 5, 7, 9, and 11, were quantified by use of an Image Analyzer (Life Science Resources VISTA, Ver. 3.0). The formulation of 1% lotion of valproate and vehicle at a dose of 200 μg/mouse, 1% valproate gel and placebo at a dose of 20 mg/mouse and 1% valproate cream and placebo at a dose of 50 mg/mouse were applied topically immediately following injury and once daily thereafter for a total of 10 consecutive days. The wounds half-closure time (CT50) was determined by linear regression using Graph-Pad Prism (Graph Pad Software USA) and unpaired Student's t test was applied for comparison between treated and vehicle group at each measurement time point. Differences were considered statistically significant at $p<0.05$ (*). The results are shown in Tables 5A-5C.

TABLE 5A (cream)

| Compound | N = 5 | Closure of wounds (%) | | | $CT_{50}$ |
|---|---|---|---|---|---|
| | | Day 3 | Day 5 | Day 7 | Days |
| Placebo | Mean | 9.9 | 2.9 | 22.4 | 12.9 |
| | SEM | 4.8 | 4.0 | 3.6 | 1.9 |
| 1% valproate cream | Mean | 9.6 | 9.9* | 33.6* | 9.8* |
| | SEM | 4.3 | 3.5 | 5.6 | 0.6 |

The valproate cream (1%, 50 mg/mouse) and vehicle (50 mg/mouse) were applied topically immediately following injury and once daily for 10 consecutive days. The wound half-closure time (CT50) was determined and unpaired Student's t test was applied for comparison between treated and vehicle group on day 3, 5, 7, 9 and 11.
Differences are considered significant at *P < 0.05.

TABLE 5B (gel)

| Com-pound | N = 5 | Closure of wounds (%) | | | | | $CT_{50}$ |
|---|---|---|---|---|---|---|---|
| | | Day 3 | Day 5 | Day 7 | Day 9 | Day 11 | Days |
| Placebo | Mean | 7.0 | 12.6 | 31.3 | 42.7 | 50.5 | 13.5 |
| | SEM | 5.0 | 5.6 | 5.5 | 5.3 | 5.7 | 1.3 |
| 1% valproate gel | Mean | 25.5** | 34.2** | 42.7** | 55.4** | 60.3** | 7.9** |
| | SEM | 3.8 | 2.0 | 2.8 | 2.8 | 2.5 | 0.5 |

The valproate gel (1%, 20 mg/mouse) and vehicle (20 mg/mouse) were applied topically immediately following injury and once daily for 10 consecutive days. The wound half-closure time (CT50) was determined and unpaired Student's t test was applied for comparison between treated and vehicle group on day 3, 5, 7, 9 and 11.
Differences are considered significant at *P < 0.05, **P < 0.01.

TABLE 5C (lotion)

| Com-pound | N = 5 | Closure of wounds (%) | | | | | $CT_{50}$ |
|---|---|---|---|---|---|---|---|
| | | Day 3 | Day 5 | Day 7 | Day 9 | Day 11 | Days |
| Placebo | Mean | 22.0 | 40.1 | 45.2 | 51.5 | 61.6 | 12.7 |
| | SEM | 2.9 | 2.2 | 2.7 | 2.8 | 2.1 | 2.2 |
| lotion | Mean | 25.3 | 41.8 | 59.9** | 71.4** | 81.8** | 6.1** |
| | SEM | 2.2 | 2.7 | 2.2 | 2.4 | 3.5 | 0.2 |
| CGS-21680 | Mean | 38.8* | 51.6* | 58.0** | 71** | 79.6** | 6.2** |
| | SEM | 3.7 | 2.7 | 3.8 | 5.0 | 8.5 | 0.5 |

Lotion (1% of valproate, 200 µg/20 µl/mouse) and vehicle (1.5% carboxymethylcellulose in PBS pH 7.4, 20 µl/mouse) as well as positive control CGS-21680 (20 µg/20 µl/mouse, Montesinos MC, et al., 1997, J. Exp. Med. 186: 1615–1620) were applied topically immediately after injury and once daily for 10 consecutive days. The wound half-closure time (CT50) was determined and unpaired Student's t test was applied for comparison between treated andvehicle group on day 3, 5, 7, 9 and 11.
Differences are considered significant at *P < 0.05, **P < 0.01.

Referring to Table 5A-5C, significant activity (p<0.05) is observed on the formulation of 1% valproate lotion since Day 7, 1% valproate gel since day 5 and 1% valproate cream since day 7, indicating the formulations of the invention are effective in treating abrasive wounds.

Example 13

Co-Administration of Trichostatin A (TSA) Ganciclovir (GCV), and Radiation (RT) Selectively Kill the Epstein-Barr Virus (EBV)-Infected Cells HDAC inhibitor as a gene modulator may up-regulate EBV thimidine kinase activity to render EBV-associated tumor killing by ganciclovir (GCV), which can be phosphorylated by EBV thymidine kinase to inhibit cellular DNA polymerase to cause cell death in S phase of cell cycle. Because HDAC inhibitor also acts as an antiproliferative agent and radiosensitizer, the combination therapies of TSA, GCV and radiation (RT) may have therapeutic benefits on eradication of EBV-infected cells or tumors such as nasopharyngeal carcinoma, cutaneous lymphoma, Hodgkin's lymphoma, X-linked lymphoproliferative disease, AIDS-related non-Hodgkin's lymphoma, and smooth muscle tumors in immunosuppressed children, which might promote the wound healing in the virus-related or -induced dermal, oral, or genital ulcers.

For EBV thimidine kinase activity assay, an equal amount of cytosol fraction was incubated with reaction buffer (50 mM Tris-HCl pH 7.4, 1 mg/ml BSA, 3 mM creatine phosphate, 11.2 U/ml creatine phosphokinase, 0.1 µM [3H-8]-GCV (specific activity 13.5 Ci/mmol), 2.5 mM ATP, 2.5 mM MgCl12, 10 mM NaF, 10 mM DTT) at 37 oC for 30 mins. The reaction mixtures were added on WhatmanR DE-81 ion exchange chromatography papers, which were then washed with 1.5 mM NH4COOH three times to remove unphosphorylated form of [3H-8]-GCV. After air drying, these papers were incubated with liquid scintillation cocktail overnight. The phosphorylation form of [3H-8]-GCV bound on WhatmanR DE-81 ion exchange chromatography paper was measured by LS6500 scintillation counter (Beckman).

Figure 10A:
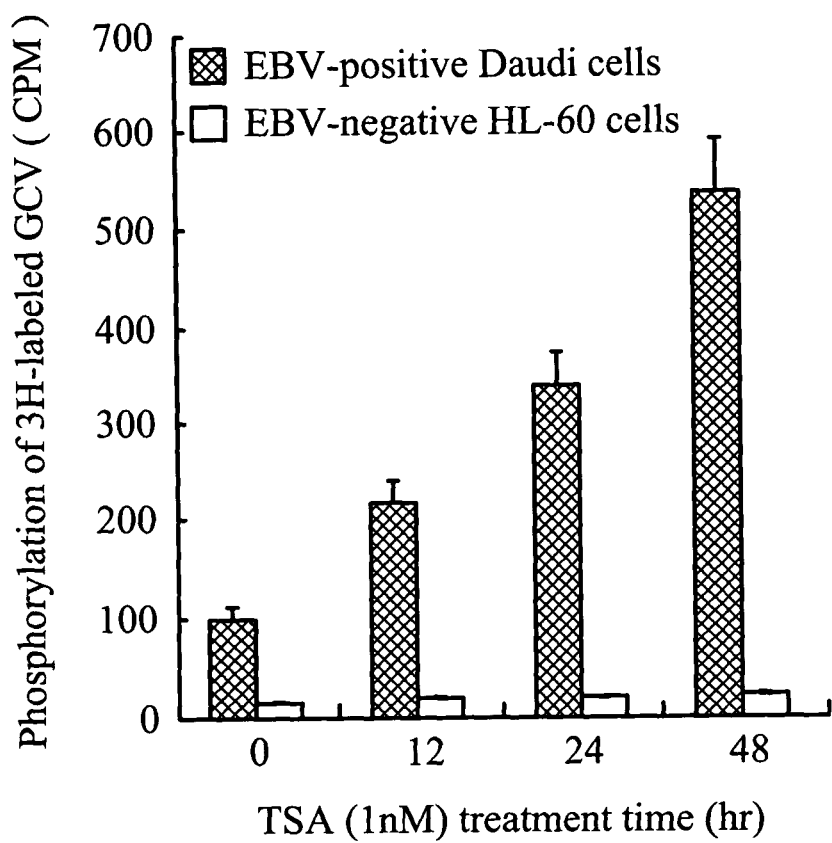
FIGS. 10A-10B show that Epstein-Barr virus (EBV)-positive Daudi's lymphoma cells were selectively destroyed but EBV-negative HL-60 leukemia cells were not by the low dose of combination of HDAC inhibitor, antibiotic and radiation.
Figure 10B:
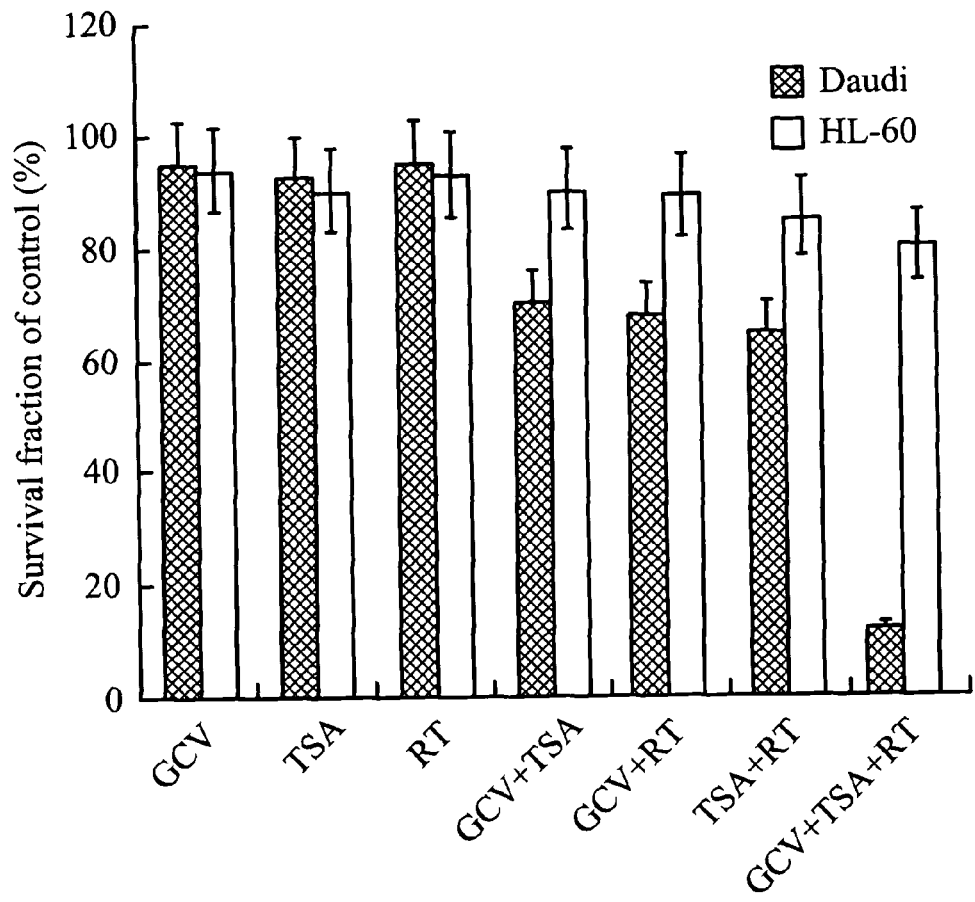

As shown in FIG. 10A, the EBV thymidine kinase activity was up-regulated by TSA 1 nM treatment for 48 hours. The combination of TSA and GCV, or TSA, GCV and radiation produced selective cell death in EBV-positive cells but not in EBV-negative cells (FIG. 10B). Daudi cells (EBV+) and HL-60 (EBV-) were treated with ganciclovir (GCV) (10 µg/ml) and/or trichostatin A (TSA) (1 nM) for 48 hours, then radiated with or without 1 Gy radiation (RT). Viable cells were counted 1 week later.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally and functionally analogous to histone deacetylase inhibitors described above can also be used to practice the present invention. Thus, other embodiments are also within the claims.

What is claimed is:

1. A method for promoting a wound healing process in skin, mucosa, or cornea, comprising applying to a wound in a subject in the inflammation phase or the tissue forming phase of the wound healing process a pharmaceutical composition including a therapeutically effective amount of a histone deacetylase inhibitor or a pharmaceutically acceptable salt thereof and a pharmaceutically acceptable carrier, wherein the histone deacetylase inhibitor is selected from the group consisting of trichostatin A, trichostatin C, sodium butyrate, isovalerate, valerate, 4-phenylbutyrate, sodium phenylbutyrate, propionate, butyramide, isobutyramide, phenylacetate, 3-bromopropionate, valproic acid, valproate, and tributyrin, and wherein the wound is selected from the group consisting of ulcer resulting from a chemical injury, phototoxic reactions, ulcer from an infectious process, desquamation resulting from drug eruption, oral aphthae, contact and irritant stomatitis, and dental erosion.

2. The method of claim 1, wherein the pharmaceutical composition is administered non-orally.

3. The method of claim 1, wherein the histone deacetylase inhibitor is present in an amount of from about 0.0001% to about 100% by weight of the composition.

4. The method of claim 1, wherein the pharmaceutical composition is a cream, an ointment, a gel, a paste, a powder, an aqueous solution, a spray, a suspension, a dispersion, a salve, a lotion, a patch, a suppository, a liposome formation, a mouth wash, an enema, an injection solution, an eye drop, an ear drop, a drip infusion, a microcapsule, or a nanocapsule.

5. The method of claim 1, wherein the pharmaceutical composition further comprises at least one agent selected from the group consisting of a cytokine, an interleukin, a growth factor, an angiogenic agent, an anti-neoplastic agent, an anti-inflammatory agent, a steroid, an immunosuppressive agent, an analgesic agent, an antipruritic agent, an antibacterial agent, an antiviral agent, an antifungal agent, an antiparasitic agent, an anti-oxidant agent, retinoic acid, an anti-fibrogenic agent, a vasoactive agent, an antibody, a conjugated antibody, an adenosine receptor agonist, and a peroxisome proliferating activator receptor (PPAR) agonist.

6. The method of claim 5, wherein the growth factor is selected from the group consisting of epidermal growth factor (EGF), fibroblast growth factor (FGF), keratinocyte growth factor (KGF), transforming growth factor-alpha (TGF-α), transforming growth factor-beta (TGF-β), platelet-derived growth factor (PDGF), vascular endothelial growth factor (VEGF), insulin-like growth factor (IGF), and granulocyte macrophage-colony stimulating factor (GM-CSF).

7. The method of claim 5, wherein the cytokine is selected from the group consisting of interleukin-1, tumor necrosis factor-alpha (TNF-α), and interleukin-6.

8. The method of claim 5, wherein the angiogenic agent is selected from the group consisting of VEGF, TGF-β, basic FGF, angiogenin, angiopoietin 1, and thrombospondin.

9. The method of claim 5, wherein the anti-oxidant agent is vitamin C, vitamin E, or superoxide dismutase.

10. The method of claim 5, wherein the anti-inflammatory agent is selected from the group consisting of corticosteroids, nonsteroidal anti-inflammatory drugs (NSAIDs), cyclosporine, colchicines, D-penicillamine, and TNF-α antagonists.

11. The method of claim 5, wherein the anti-fibrogenic agent is selected from the group consisting of interferons, TGF-β antagonists, and angiotensin-converting enzyme inhibitors.

12. The method of claim 5, wherein the antiviral agent is Ganciclovir, Acyclovir, or Famciclovir.

13. The method of claim 1, wherein the subject is a human, a dog, a cat, a rat, a hamster, or a mouse.

14. The method of claim 1, wherein the applying step is performed in the inflammation phase.

15. The method of claim 1, wherein the applying step is performed in the tissue forming phase.

\* \* \* \* \*